US009844217B2

(12) United States Patent
Pageat

(10) Patent No.: US 9,844,217 B2
(45) Date of Patent: *Dec. 19, 2017

(54) ALLOMONE REPULSIVE AND KAIROMONE ATTRACTIVE COMPOSITIONS FOR CONTROLLING ARACHNIDS

(71) Applicant: Fideline, Saint-Saturnin D'apt (FR)

(72) Inventor: Patrick Pageat, Route de Saint-Saturnin (FR)

(73) Assignee: Institut de Recherche en Semiochimie et Ethologie Appliquée, Apt (FR)

( * ) Notice: Subject to any disclaimer, the term of this patent is extended or adjusted under 35 U.S.C. 154(b) by 353 days.

This patent is subject to a terminal disclaimer.

(21) Appl. No.: 14/321,294

(22) Filed: Jul. 1, 2014

(65) Prior Publication Data

US 2014/0316000 A1    Oct. 23, 2014

Related U.S. Application Data

(63) Continuation of application No. 11/003,530, filed on Dec. 6, 2004, now Pat. No. 8,828,921, which is a continuation of application No. PCT/EP03/07143, filed on Jun. 19, 2003.

(60) Provisional application No. 60/390,059, filed on Jun. 19, 2002.

(30) Foreign Application Priority Data

Jun. 19, 2002  (EP) .................................... 02291534

(51) Int. Cl.
| | |
|---|---|
| A01N 37/06 | (2006.01) |
| A01N 27/00 | (2006.01) |
| A01N 31/02 | (2006.01) |
| A01N 37/04 | (2006.01) |
| A01N 37/12 | (2006.01) |
| A01N 63/02 | (2006.01) |
| A61K 35/55 | (2015.01) |
| A01N 37/02 | (2006.01) |
| A01N 37/14 | (2006.01) |
| C07C 47/02 | (2006.01) |
| C07C 69/02 | (2006.01) |

(52) U.S. Cl.
CPC ............ *A01N 37/06* (2013.01); *A01N 27/00* (2013.01); *A01N 31/02* (2013.01); *A01N 37/02* (2013.01); *A01N 37/04* (2013.01); *A01N 37/12* (2013.01); *A01N 37/14* (2013.01); *A01N 63/02* (2013.01); *A61K 35/55* (2013.01); *C07C 47/02* (2013.01); *C07C 69/02* (2013.01)

(58) Field of Classification Search
CPC .......... A01N 27/00; C07C 47/02; C07C 69/02
See application file for complete search history.

(56) References Cited

U.S. PATENT DOCUMENTS

| | | | |
|---|---|---|---|
| 4,853,217 A | 8/1989 | Francke | |
| 5,882,636 A | 3/1999 | Mui et al. | |
| 6,391,943 B2 | 5/2002 | Sarma et al. | |
| 6,500,416 B2 | 12/2002 | Hofer et al. | |
| 2001/0021378 A1 | 9/2001 | Hofer et al. | |

FOREIGN PATENT DOCUMENTS

| | | |
|---|---|---|
| JP | 4108171 | 4/1992 |
| JP | 9169608 | 6/1997 |
| JP | 20000302607 | 10/2000 |

OTHER PUBLICATIONS

Bohnet, S., et al., "Estradiol Induces Proliferation of Peroxisome-like Microbodies and the Production of 3-Hydroxy Fatty Acid Diesters, the Femal Pheromones, in the Uropygial Glands of Male and Female Mallards," Journal of Biological Chemistry, 266:9795-9804 (1991).
Cheesbrough, T., et al., "Microsomal Preparation from an Animal Tissue Catalyzes Release of Carbon Monoxide from a Fatty Aldehyde to Generate an Alkane," Journal of Biological Chemistry, 263:2738-2743 (1988).
Sato, M., et al., "Male and Female Sex Pheromones Produced by Acarus immobilis Griffiths (Acaridae: Acarina)," Naturwissenschaften, 80:34-36 (1993).
Zeman, P., "Surface Skin Lipids of Birds—a Proper Host Kairomone and eeding Inducer in the Poultry Red Mite, Dermanyssus gallinae," Experimental & Applied Acarology, 5:163-174 (1988).
Morr, M. et al., "Synthesis of Asymmetrical Methyl-Branched Chiral Ketones from the Corresponding Homologous Wax Esters, A New Synthesis of the Insect Pheromone Lardolure and of 9-Norlardolure," Liebigs Ann. 1995, 2001-2004.
Hiremath, L.S. et al., "Estrogen induction of alcohol dehydrogenase in the uropygial gland of mallard ducks," Eur. J. Biochem. 203, 449-457, 1992.
Act on the Evaluation of Chemical Substances and Regulation of Their Manufacture, etc., Chemical Profile, 2,2,4-Trimethyl-1, 3-pentanedioldiisobutyrate, CAS 6846-50-0, EINECS 229-934-9, with English translation.

*Primary Examiner* — Kyle Purdy
(74) *Attorney, Agent, or Firm* — Venable LLP; Keith G. Haddaway

(57) ABSTRACT

Composition of allomones and kairomones derived from the uropygeal gland of ducks and chickens are described, as well as methods to treat Arachnids.

30 Claims, 26 Drawing Sheets

ALLOMONE REPULSIVE AND KAIROMONE ATTRACTIVE COMPOSITIONS FOR CONTROLLING ARACHNIDS

CROSS REFERENCE TO RELATED APPLICATION

This application is a continuation of U.S. application Ser. No. 11/003,530, filed Dec. 6, 2004, which is a continuation of International Application No. PCT/EP2003/007143, filed Jun. 19, 2003, and which claims priority from European Patent Application No. 02291534.2, and claims the benefit of U.S. Provisional Application No. 60/390,059, both filed on Jun. 19, 2002, all of which are hereby incorporated by reference in their entirety.

The present invention relates to compositions of allomones and kairomones derived from the uropygial gland of ducks and chickens to treat Arachnida.

PRIOR ART

Arachnida are a class of arthropods allied to insects and crustaceans, but having eight legs, no wings or antennae, two body regions and a breathing mechanism of a tracheal tube or a pulmonary source. Included in the class of arachnids are spiders, mites, ticks, daddy long legs and scorpions.

Particular arachnids are a nuisance for vertebrates. As an example, the black widow spider is venomous and is fifteen times as toxic as the venom of the prairie rattlesnake. The black widow spider has no particular host preferences and therefore will bite any subject. Although in many instances, the venom from a bite of a black widow spider is not mortal, there still exists some cases in which mortality has occurred in young or very old individuals.

This is in contrast to ticks in which mice and deer are the most commonly infected animals which serve as hosts to ticks. It is well known that ticks are the cause of Lyme disease which causes an acute inflammatory disease characterized by skin changes, joint inflammation and flu-like symptoms caused by the bacterium *Borrelia burgdorferi* transmitted by the bite of a deer tick. It is well known that Lyme disease has been linked to a chronic syndrome of diffuse aches, pains, memory trouble and various other medical problems that can occur over months and even years in humans. The number of cases of Lyme disease has risen over the last few years and in the United States alone, a record high of 17,730 cases were reported in the year 2000.

Yet another category of arachnids are mites, which are parasitic and host specific. Certain mites migrate from birds, rodents, food material, vegetable matter and house dust and can attack and annoy humans. There are different categories of mites including Northern fowl mites (*Ornithonyssus sylviarum*), chicken mites (*Dermanyssus gallinae*), tropical rat mites (*Ornithonyssus bacoti*), house mouse mites (*Liponyssoides sanuineus*), follicle mites (*Demodex folliculorum*), itch or scabies mites (*Sarcoptes scabiei hominis*), straw itch mites (*Pyemotes tritici*), grain (*Acarus siro* L.) and mold mites (*Tyrophagus putrescentiae*) and house dust mites (*Dermatophagoides* sp.).

Mites also infect a variety of other animals. The adults can be found in a variety of locations, while the eggs are usually deposited on the soil surface, in cracks and crevices and in some instances under the skin of the host they infest. Burrowing mange mites (*Sarcoptes scabiei*), as well as non-burrowing mange mites (*Chorioptes bovis*) are known to infest many animals including man. Feline mange mites (*Notoedres cati*), though fairly rare are highly contagious and infect kittens, cats and rabbits. *Psoroptes ovis* is the mite that infects sheep. *Psoroptes bovis* is the mite that infects cattle and *Psoroptes cuniculi* is the mite that infects rabbits. The *Psoroptes* group of mites causes scabies in the animals infected.

*Demodex folliculorum*, the cigar-shaped mite causes canine demodecosis. This skin disease in dogs is difficult to treat since symptoms on the skin may result in either a scaly form or a pustular form. Generally repeated treatment with antibiotics and antihistamines is required. *Dermanyssus gallinae*, commonly known as chicken mites or red chicken mites, is the red mite of poultry and commonly feeds on birds only at night. Cats and dogs may become infected as a result of contact with the poultry.

For instance, pet birds, kittens, cats and rabbits also can be infested with mites. It has recently been reported that pet gerbils have also become infested with Northern Fowl mites and chicken mites. The blood sucking mites can also transmit encephalitis and may cause fowl mite dermatitis and acariasis.

Mites are parasitic and can feed on their host sucking their blood and causing anemia, itching, dermatitis and scabies. Their parasitic nature causes certain mites to be a menace, not only for humans, but especially for certain industries such as the poultry industry.

It is well known that Northern Fowl mites (*Ornithonyssus sylviarum*) is an external parasite of poultry with heavy populations capable of reducing egg production up to 10% to 15%. The entire life cycle can be completed on a bird and consists of egg, larva, nymphal stages and adult. The eight legged adult is about 1/26 inch long and is dark red to black in color. The entire life cycle can be completed within one week.

Besides the Northern Fowl mite, the chicken mite (*Dermanyssus gallinae*) sucks blood from poultry during the night and remains secluded during the day. These mites are generally gray in color and turn red after feeding. These mites can be barely seen without a magnifying glass. When there is a serious infestation of mites, weight gains in various poultry is reduced, as well as egg production. In some instances with a large infestation of mites young birds and setting hens may actually die from mite-induced anemia.

Mite infestation in poultry farming is a serious problem and results in not only loss of egg production, but also loss of the broiler chickens themselves. The poultry industry presently finds themselves loosing vast amounts of money due to the infestation of mites. There is no easy solution to this problem, since in many cases hygienic alimentation requires that all chemical products used to kill mites cannot be used in the presence of live poultry.

Many chemical products are available to treat the problem of mites. These products include Actograd (Virbac), Tugon 80 (Bayer), Sebacil (Bayer) and Etcodex (Hoechst), to mention a few miticides. But, as mentioned above, these products cannot be used in the presence of poultry and thus the chicken breeder must remove the chickens and hens from their housing when using these products.

Besides miticides, there are other alternatives to treat mites and various other arachnids. These treatments include treatment by gas to disinfect the poultry houses and use of silica powder. However, the former method is quite costly and requires that the poultry be housed in a different environment during treatment. Also, the gaseous molecules used in this treatment are often injurious to the health of humans and animals. The silica powder treatment can be done in the presence of the poultry, but requires a very strong dosage and one is obliged to saturate the silica powder throughout the poultry houses. Moreover, silica powder is known to cause a number of lung diseases both in birds and in man.

One of the most prominent problems with chemical and silica powder treatment is that mites are known to inhabit in cracks and crevices of the poultry houses and hence are difficult to kill using chemical miticides and silica powder treatment.

Due to the infestation of mites in poultry the poultry farmers loose between 10% to 40% of their business. Once the mites are present in a flock it is impossible to exterminate the mites in one attempt with a treatment. In fact, in the United States when a poultry house is infested with mites on a scale of 10 for more than four months, the average rate being 8, the poultry or hen house is completely destroyed. After destruction of the poultry or hen house, the ground in which the house was built, as well as 400 meters surrounding it, is then sterilized and a new poultry house is then built. One can appreciate that this procedure, although quite efficient to rid the mite infestation, is very costly.

Thus, there is a need in this art to find a better solution to the problem of treating arachnids and especially *Dermanyssus gallinae* in the poultry industry, while not harming other animals or man.

The secretions produced by different glands that can intervene in a chemical communication are known as chemical signals. Amongst the chemical signals are those that participate strictly in intraspecific communications, which can be distinguished from those that are implicated in the interspecific communications.

Those chemical signals that participate in intraspecific communications are called pheromones. By definition, pheromones are substances released by the body that cause a predictable reaction by another individual of the same species, which substance may serve, for example, as a specific attractant, social communicator, sexual stimulant and the like. A number of different glands are known to produce pheromones in male mammals such as the submaxillary, salivary glands, the parathyroid glands and the sebaceous glands. Various applications of pheromones are described in U.S. Pat. Nos. 6,054,481, 6,077,867 and 6,169,113.

Those chemical signals that participate in interspecific communications are grouped under the general category of allelochemical signals.

The allelochemical signals are generally divided into two subgroups and their function affects the relationship between the emitter of the signal and the receiver of the message. When there is a chemical signal that is emitted, that in relation to the favorable emitter, the sub grouping is known as an allomone. By definition, an allomone is a hormone or substance produced by one species that has an effect upon another species, especially so as to benefit the emitting species. For example, attractive allomones emitted by certain flowers can attract various insects that can pollinate these flowers.

In contrast when the chemical signal emitted is in relation favorable to the receiver the sub grouping is known as a kairomone. A kairomone, by definition, is a pheromone or substance that can attract other species and sometimes even natural enemies. The kairomones are sometimes implicated in locating a particular host by a parasite. For example, lactic acid that is emitted by human skin is a kairomone known for a number of Culicidae.

Allomones and kairomones are natural substances that degrade causing no harm to the end user. These chemicals also do not cause immunity and are safe.

Thus, in one aspect the present invention provides a duck repulsive allomone and a chicken attractive kairomone, which can be used to treat arachnid infestations and which are safe and effective and can be used in the presence of other animals, including humans.

In another aspect the present invention provides a duck repulsive allomone that can be used to treat or prevent poultry infection with chicken mites or Northern fowl mites.

In yet another aspect, the present invention provides a chicken attractive kairomone that can be used in conjunction with an adhesive material to trap chicken mites or Northern fowl mites.

In yet another aspect the present invention relates to a method of treating or preventing chicken mites or Northern fowl mites in birds such as hens, chickens, turkeys, ducks, geese and young chicks said method comprising administering to hens, chickens or young chicks in need of such treatment a pharmaceutically effective amount of a duck *Dermanyssus* repulsive allomone.

These and other objects are achieved by the present invention as evidenced by the summary of the invention, description of the preferred embodiments and the claims.

SUMMARY OF THE INVENTION

The present invention thus relates to a duck repulsive allomone or a chicken attractive kairomone. The allomones and kairomones were derived from the uropygial gland of ducks and chickens, respectively.

The duck repulsive allomone composition of the present invention can be used to repulse arachnids such as spiders, ticks and mites and thus prevents these arachnids from biting or feeding on hosts.

In another aspect the present invention provides a kairomone composition which can be used to attract arachnids. Once the arachnids are attracted to this kairomone that can be further trapped using an adhesive material or to induce the mite to feed on a miticide that is in the trap. The kairomone induces the feeding behavior and thus it is possible to enhance the mite to stick on any kind of adhesive surface such as, for example, polyethylene films.

In another aspect the present invention provides a duck repulsive allomone comprising bis(2-ethylhexyll) adipate and 2,2,4-trimethyl 1,3 pentanediol diisobutyrate and/or derivatives thereof and/or isomers thereof, as well as mixtures of bis(2-ethylhexyll) adipate or 2,2,4-trimethyl 1,3 pentanediol diisobutyrate with one or more derivatives with one or more isomers of bis(2-ethylhexyll) adipate or 2,2,4-trimethyl 1,3 pentanediol diisobutyrate and/or one or more isomers of the derivatives of bis(2-ethylhexyll) adipate or 2,2,4-trimethyl 1,3 pentanediol diisobutyrate.

In another aspect the present invention provides a duck repulsive allomone composition comprising about 45.0 to 55.0 (w %/w %) of bis(2-ethylhexyll) adipate and about 45.0 to 55.0 (w %/w %)2,2,4-trimethyl 1,3 pentanediol diisobutyrate and/or esters, or salts, alcohols, ketones, ethers, aldehydes, sterols and amides derivatives of bis(2-ethylhexyll) adipate and 2,2,4-trimethyl 1,3 pentanediol diisobutyrate and/or isomers of bis(2-ethylhexyll) adipate and 2,2,4-trimethyl 1,3 pentanediol diisobutyrate and their derivatives, as well as mixtures of bis(2-ethylhexyll) adipate or 2,2,4-trimethyl 1,3 pentanediol diisobutyrate with one or more esters, or salts, alcohols, ketones, ethers, aldehydes, sterols and amides derivatives of bis(2-ethylhexyll) adipate and 2,2,4-trimethyl 1,3 pentanediol diisobutyrate with one or more isomers of bis(2-ethylhexyll) adipate and 2,2,4-trimethyl 1,3 pentanediol diisobutyrate and/or one or more isomers of their derivatives.

In another aspect the present invention provides a chicken attractive kairomone composition comprising 1-heptadecene, hepatdecane, 9-octadecene-ol 1 (oleyl alcohol), octadecane and/or derivatives thereof and/or isomers thereof, as well as mixtures of one or more of 1-heptadecene, hepatdecane, 9-octadecene-ol 1 (oleyl alcohol), octadecane with one or more derivatives of 1-heptadecene, hepatdecane, 9-octadecene-ol 1 (oleyl alcohol), octadecane with one or more isomers of 1-heptadecene, hepatdecane, 9-octadecene-ol 1 (oleyl alcohol), octadecane and/or one or more isomers of the derivatives of 1-heptadecene, hepatdecane, 9-octadecene-ol 1 (oleyl alcohol), octadecane.

In another aspect the present invention provides a chicken attractive kairomone composition comprising about 23.5 to 26.5 (w %/w %) of 1-heptadecene, about 23.5 to 26.5 (w %/w %) of hepatdecane, about 23.5 to 26.5 (w %/w %) of 9-octadecene-ol 1 (oleyl alcohol) and about 23.5 to 26.5 (w %/w %) of octadecane and/or esters, or salts, alcohols, ketones, ethers, aldehydes, sterols and amides derivatives of 1-heptadecene, hepatdecane, 9-octadecene-ol 1 (oleyl alcohol) and octadecane, and/or isomers thereof, as well as mixtures of one or more of 1-heptadecene, hepatdecane, 9-octadecene-ol 1 (oleyl alcohol), octadecane with one or more esters, or salts, alcohols, ketones, ethers, aldehydes, sterols and amides derivatives of 1-heptadecene, hepatdecane, 9-octadecene-ol 1 (oleyl alcohol) and octadecane with one or more isomers of 1-heptadecene, hepatdecane, 9-octadecene-ol 1 (oleyl alcohol), octadecane and/or one or more isomers of the derivatives of 1-heptadecene, hepatdecane, 9-octadecene-ol 1 (oleyl alcohol), octadecane.

The allomone or the kairomone compositions described above can have varying concentrations of 0.1% to 99.9%. However an increased effect is present when using the specific concentrations described herein. Moreover in the kairomone composition, at least two of the compounds selected from 1-heptadecene, hepatdecane, 9-octadecene-ol 1 (oleyl alcohol) and octadecane can be used in the formulation and still possess a kairomone effect.

In another aspect the present invention relates to a method of repulsing Arachnids, said method comprising administering a repulsing amount of a duck repulsive allomone to an animal in need of such treatment.

A method of repulsing arachnids said method comprising administering to a human in need of such treatment a pharmaceutically acceptable amount of a duck repulsive allomone. These arachnids include, but are not limited to, *Dermanyssus gallinae*, a tick or an *Ornithonyssus*.

In another aspect, present invention also relates to a method of treating or preventing chicken mites or Northern fowl mites in hens, chickens, ducks, geese, turkeys, and young chicks said method comprising administering to hens, chickens or young chicks in need of such treatment a pharmaceutically effective amount of a duck repulsive allomone comprising about 45.0 to 55.0 (w %/w %) of bis(2-ethylhexyll) adipate and about 45.0 to 55.0 (w %/w %)2,2,4-trimethyl 1,3 pentanediol diisobutyrate and/or derivatives thereof and/or isomers thereof, as well as mixtures of bis(2-ethylhexyll) adipate or 2,2,4-trimethyl 1,3 pentanediol diisobutyrate with one or more esters, or salts, alcohols, ketones, ethers, aldehydes, sterols and amides derivatives of bis(2-ethylhexyll) adipate and 2,2,4-trimethyl 1,3 pentanediol diisobutyrate with one or more isomers of bis(2-ethylhexyll) adipate and 2,2,4-trimethyl 1,3 pentanediol diisobutyrate and/or one or more isomers of the derivatives of bis(2-ethylhexyll) adipate and 2,2,4-trimethyl 1,3 pentanediol diisobutyrate.

In yet another aspect the present invention relates to a method of attracting *Dermanyssus* in buildings or hen houses comprising placing an attractive kairomone comprising about 23.5 to 26.5 (w %/w %) of 1-heptadecene, about 23.5 to 26.5 (w %/w %) of hepatdecane, about 23.5 to 26.5 (w %/w %) of 9-octadecene-ol 1 (oleyl alcohol) and about 23.5 to 26.5 (w %/w %) of octadecane, as well as mixtures of one or more of 1-heptadecene, hepatdecane, 9-octadecene-ol 1 (oleyl alcohol), octadecane with one or more esters, or salts, alcohols, ketones, ethers, aldehydes, sterols and amides derivatives of 1-heptadecene, hepatdecane, 9-octadecene-ol 1 (oleyl alcohol) and octadecane with one or more isomers of 1-heptadecene, hepatdecane, 9-octadecene-ol 1 (oleyl alcohol), octadecane and/or one or more isomers of the derivatives of 1-heptadecene, hepatdecane, 9-octadecene-ol 1 (oleyl alcohol), octadecane in the building or hen house thereby attracting *Dermanyssus*.

PREFERRED EMBODIMENTS OF THE PRESENT INVENTION

Figure 1:
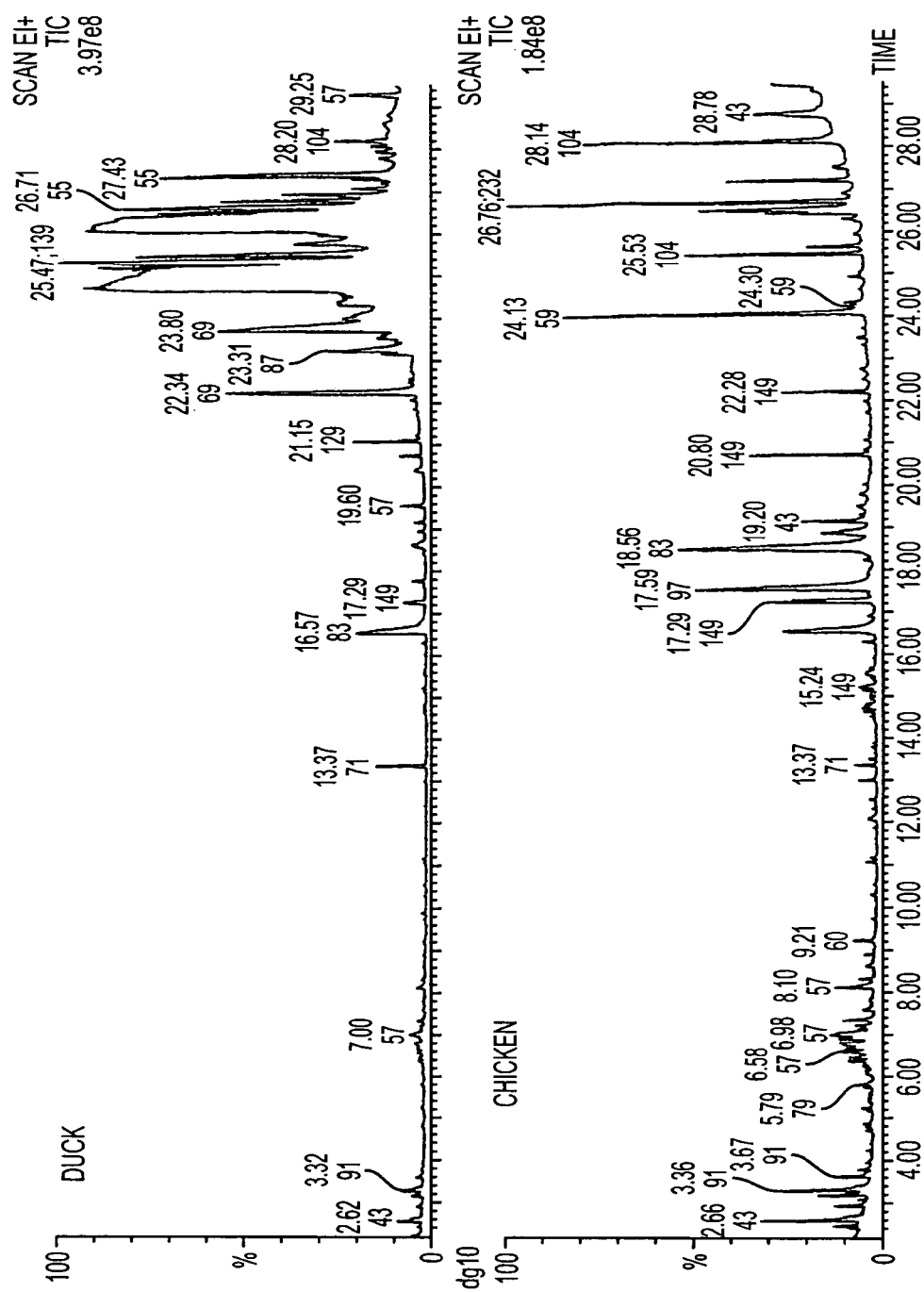
FIG. 1 is a gas chromatography/mass spectroscopy spectrum profile of the components found in the secretions of ducks and chickens from the uropygial gland.

As used herein, the term "arachnids" encompasses all of the class Arachnida including the order Arachnida, Parasitiformes and Acarini. Thus, included in the class Arachnida are spiders, ticks, as well as all types of mites, including the suborders of Mesostigmata, Astigmata and Prostigmata.

As used herein, the word "bird" and "avian" are used interchangeably and encompass any warm-blooded animal with feathers and wings that lays eggs and is usually able to fly. Examples of birds, includes, but is not limited to chicks, chickens, hens, ducks, geese, turkeys and the like.

By "kairomone" is meant a semiochemical that is produced by one organism to induce a response in an organism of another species. It produces a response that is unfavorable to the emitter.

By "allomone" is meant a semiochemical that is produced by one organism to induce a response in an organism of another species. It produces a response favorable to the emitter. For example, some plants produce allomones that repel insects and keep them from feeding.

By the term "solution" is meant a solid that is dispersed through a liquid either by being dissolved in it or being in suspension.

By "enhancer composition" is meant an active composition that is species-species specific in birds and which can be used to enhance or act synergistically with the allomone or kairomone composition to increase the effectiveness in specific species of the composition.

When referring to the mixtures of the compounds set forth in the present invention with one or more of their derivatives and one or more isomers means that the composition can include, for example only, bis(2-ethylhexyll) adipate and an alcohol derivative of 2,2,4-trimethyl 1,3 pentanediol diisobutyrate or an alcohol derivative of bis(2-ethylhexyll) adipate and an isomer of the alcohol derivative of 2,2,4-trimethyl 1,3 pentanediol diisobutyrate. The derivatives and isomers referred to herein have the exact same weight percentages as mentioned by their chemical counterparts. For example, the derivatives and isomers of from about 45.0 to 55.0 (w %/w %) bis(2-ethylhexyl)adipate and from about 45.0 to 55.0 (w %/w %). 2,2,4-trimethyl 1,3 pentanediol diisobutyrate have the same concentration of from about 45.0 to 55.0 (w %/w %). The same rationale also applies to the kairomone composition.

As used herein the term "isomers" includes structural isomerism and spatial isomerism and refers to the isomers of the allomone composition and kairomone composition, as well as their derivatives.

More specifically, the present invention relates to the identification of an allomone composition and a kairomone composition that is derived from secretions around the uropygial gland of birds.

The allomone composition of the present invention comprises a mixture of bis(2-ethylhexyl) adipate and 2,2,4-trimethyl 1,3 pentanediol diisobutyrate and/or derivatives thereof and/or isomers thereof and/or mixtures of bis(2-ethylhexyll) adipate or 2,2,4-trimethyl 1,3 pentanediol diisobutyrate with one or more esters, or salts, alcohols, ketones, ethers, aldehydes, sterols and amides derivatives of bis(2-ethylhexyll) adipate and 2,2,4-trimethyl 1,3 pentanediol diisobutyrate with one or more isomers of bis(2-ethylhexyl) adipate and 2,2,4-trimethyl 1,3 pentanediol diisobutyrate and/or one or more isomers of the derivatives of bis(2-ethylhexyl) adipate and 2,2,4-trimethyl 1,3 pentanediol diisobutyrate.

The allomone composition of the present invention comprises a mixture of about 45.0 to 55.0 (w %/w %) of bis(2-ethylhexyl) adipate and from about 45.0 to about 55.0 (w %/w %) of 2,2,4-trimethyl 1,3 pentanediol diisobutyrate and/or derivatives thereof and/or isomers thereof and/or mixtures of bis(2-ethylhexyll) adipate or 2,2,4-trimethyl 1,3 pentanediol diisobutyrate with one or more esters, or salts, alcohols, ketones, ethers, aldehydes, sterols and amides derivatives of bis(2-ethylhexyll) adipate and 2,2,4-trimethyl 1,3 pentanediol diisobutyrate with one or more isomers of bis(2-ethylhexyl) adipate and 2,2,4-trimethyl 1,3 pentanediol diisobutyrate and/or one or more isomers of the derivatives bis(2-ethylhexyl) adipate and 2,2,4-trimethyl 1,3 pentanediol diisobutyrate.

The kairomone composition of the present invention comprises a mixture of about 23.5 to 26.5 (w %/w %) of 1-heptadecane, about 23.5 to 26.5 (w %/w %) of hepatdecane, from about 23.5 to 26.5 (w %/w %) 9-octadecene-ol 1 (oleyl alcohol) and about 23. % to 26.5 (w %/w %) of octadecane and/or or derivatives thereof and/or isomers thereof and/or mixtures of one or more of 1-heptadecene, hepatdecane, 9-octadecene-ol 1 (oleyl alcohol), octadecane with one or more esters, or salts, alcohols, ketones, ethers, aldehydes, sterols and amides derivatives of 1-heptadecene, hepatdecane, 9-octadecene-ol 1 (oleyl alcohol) and octadecane with one or more isomers of 1-heptadecene, hepatdecane, 9-octadecene-ol 1 (oleyl alcohol) and octadecane and/or one or more isomers of the derivatives of 1-heptadecene, hepatdecane, 9-octadecene-ol 1 (oleyl alcohol) and octadecane.

The allomone or the kairomone compositions described above can have varying concentrations of 0.1% to 99.9%. However an increased effect is present when using the specific concentrations described herein. Moreover in the kairomone composition, at least two of the compounds selected from 1-heptadecene, hepatdecane, 9-octadecene-ol 1 (oleyl alcohol) and octadecane can be used in the formulation and still possess a kairomone effect.

The allomone or kairomone compositions can also be attached to a chemical carrier provided that the bioactive structure of the composition is preserved. Such carrier molecules include, but are not limited to, resins, liposomes, crown compounds, carrier proteins, any kind of polymer and the like.

The compositions can be used in their pure form, as well as their derivative form such as esters, or salts, as well as alcohols, ketones, ethers, aldehydes, sterols and amides. Isomers of the pure and derivative forms are also encompassed in the present invention. These derivatives or isomers can replace one or more or all of the chemical components in the compositions of the present invention and have the same effects.

In another aspect the present invention comprises the composition in solution. Thus, the present invention provides in solution of about 45.0 to 55.0 (w %/w %) of bis(2-ethylhexyl) adipate and from about 45.0 to about 55.0 (w %/w %) of 2,2,4-trimethyl 1,3 pentanediol diisobutyrate of a duck *Dermanyssus* repulsive allomone and/or derivatives thereof and/or isomers thereof and/or mixtures of bis(2-ethylhexyll) adipate or 2,2,4-trimethyl 1,3 pentanediol diisobutyrate with one or more esters, or salts, alcohols, ketones, ethers, aldehydes, sterols and amides derivatives of bis(2-ethylhexyll) adipate and 2,2,4-trimethyl 1,3 pentanediol diisobutyrate with one or more isomers of bis(2-ethylhexyll) adipate and 2,2,4-trimethyl 1,3 pentanediol diisobutyrate and/or one or more isomers of the derivatives of bis(2-ethylhexyll) adipate and 2,2,4-trimethyl 1,3 pentanediol diisobutyrate or about 23.5 to 26.5 (w %/w %) of 1-hepatdecane, about 23.5 to 26.5 (w %/w %) of hepatdecane, from about 23.5 to 26.5 (w %/w %) 9-octadecene-ol 1 (oleyl alcohol) and about 23.5 to 26.5 (w %/w %) of octadecane and/or derivatives and/or isomers thereof and/or mixtures of one or more of 1-heptadecene, hepatdecane, 9-octadecene-ol 1 (oleyl alcohol), octadecane with one or more esters, or salts, alcohols, ketones, ethers, aldehydes, sterols and amides derivatives of 1-heptadecene, hepatdecane, 9-octadecene-ol 1 (oleyl alcohol) and octadecane with one or more isomers of 1-heptadecene, hepatadecane, 9-octadecene-ol 1 (oleyl alcohol) and/or one or more isomers of their derivatives of a chicken *Dermanyssus* attractive kairomone.

These compositions and solutions are used separately as either a repulsive composition or an attractive composition.

The composition may be in the form of a solution, aerosol spray, gel, slow release matrix, shampoo, soap, lotion, ointment and the like. The composition can also be placed in liposomes, in a diffuser, in any kind of polymer and can be microencapsulated.

The allomone solution and compositions of the present invention can also be placed in feedstuff and be fed to the birds or other animals. It can also be placed in water and drunk by birds or other animals.

The concentration of the above-mentioned allomone and kairomone compositions may vary depending upon the final form of use. However, the concentrations of these compositions that are utilized and their concentration may be ascertained and tested according to the methods set forth in the present invention.

The allomone and kairomone compositions can be diluted in any nonaqueous solvent to form the solution of the present invention. Solvents such as, alcohol, diethyl ether, chloroform, ethanol, benzene, propyl alcohol, isopropanol, 2-propanol, acetone polysorbate 80 and the like. Combinations of these solvents can also be used.

When the compositions are administered in food, they are generally dissolved in an aqueous solution that can be ingested such as water or in vegetal or animal oil or any kind of fat product used to prepare animal or human food. They can also be added as a solid composition directly to the foodstuff.

The chicken *Dermanyssus* attractive kairomone can also be placed on sticky paper such as cellulosic paper or in a box that can attract and trap the arachnids. Besides the attractive kairomone, an adhesive is also used for entrapment purposes. Such an adhesive can be either a natural adhesive or a synthetic adhesive. Typical natural adhesives include starches and modified starches. The synthetic adhesives that can be used in the present invention include, but are not limited to polyacrylates, polyvinyl chlorides, silicones, urethanes, styrene copolymers, polyvinylacetates and the like. The adhesive layer is generally between 0.02 to 0.5 inches thick.

The entrapment box or container can be made of any material such as cardboard for interior use or plastic or polymers for exterior use. The attractive kairomone is spread throughout the interior and the container or box has one or more entry passages such that the arachnids can enter freely and be entrapped by the adhesive substance. The concentration of the kairomone is from about 0.015 ppm to 0.5 ppm in this application for the container.

The present allomone compositions can be applied to a variety of objects that Arachnids come in contact with such as walls, tents, beds, carpets, clothes and the like. Moreover, the present allomone composition can be applied topically on animals or humans to repel arachnids such as mites, ticks, spiders and the like.

The present invention also relates to a method of repulsing Arachnids, said method comprising administering a repulsing amount of a duck repulsive allomone to a animal in need of such treatment. Included in the category of animals is man, since chicken mites are zoonotic parasites and is effective to avoid feeding in humans.

The present invention includes a method of treating or preventing chicken mites or Northern fowl mites in hens, chickens, ducks, turkeys, geese and young chicks said method comprising administering to hens, chickens or young chicks in need of such treatment a pharmaceutically effective amount of a duck repulsive allomone comprising about 45.0 to 55.0 (w %/w %) of bis(2-ethylhexyll) adipate and about 45.0 to 55.0 (w %/w %)2,2,4-trimethyl 1,3 pentanediol diisobutyrate and/or derivatives thereof and/or isomers thereof and/or mixtures of bis(2-ethylhexyll) adipate or 2,2,4-trimethyl 1,3 pentanediol diisobutyrate with one or more esters, or salts, alcohols, ketones, ethers, aldehydes, sterols and amides derivatives of bis(2-ethylhexyll) adipate and 2,2,4-trimethyl 1,3 pentanediol diisobutyrate with one or more isomers of bis(2-ethylhexyll) adipate and 2,2,4-trimethyl 1,3 pentanediol diisobutyrate and/or one or more isomers of the derivatives of bis(2-ethylhexyll) adipate and 2,2,4-trimethyl 1,3 pentanediol diisobutyrate.

In yet another aspect the present invention includes a method of attracting *Dermanyssus* in buildings or hen houses comprising placing an attractive kairomone comprising about 23.5 to 26.5 (w %/w %) of 1-heptadecene, about 23.5 to 26.5 (w %/w %) of hepatdecane, about 23.5 to 26.5 (w %/w %) of 9-octadecene-ol 1 (oleyl alcohol) and about 23.5 to 26.5 (w %/w %) of octadecane and/or derivatives thereof and/or isomers thereof and/or mixtures of one or more of 1-heptadecene, hepatdecane, 9-octadecene-ol 1 (oleyl alcohol), octadecane with one or more esters, or salts, alcohols, ketones, ethers, aldehydes, sterols and amides derivatives of 1-heptadecene, hepatdecane, 9-octadecene-ol 1 (oleyl alcohol) and octadecane with one or more isomers of 1 heptadecene, hepatdecane, 9-octadecene-ol 1 (oleyl alcohol) and octadecane and/or one or more isomers of the derivatives of 1-heptadecene, hepatdecane, 9-octadecene-ol 1 (oleyl alcohol) and octadecane in the building or hen house thereby attracting *Dermanyssus*.

The above-described compositions were discovered after detailed analysis of the chemical compositions obtained from secretions of the uropygial gland in ducks and chickens.

More particularly, this procedure involved swabbing the uropygial area of ducks or chickens with a sterile compress and analyzing the composition of the secretions with gas chromatography/mass spectroscopy. From the chromatographs the chemical compositions that were prevalent in the secretions were further analyzed using a computer database, which are known in the art and the chemical make-up was determined for the allomone composition and the kairomone composition.

In order to fully illustrate the present invention and advantages thereof, the following specific examples are given, it being understood that the same are intended only as illustrative and in nowise limitative.

Example 1

Isolation and Analysis to Identify Allomones and Kairomones from Chickens and Ducks The samples were obtained from ducks and chickens by applying a sterile compress to the uropygial gland or tail gland and secretions from this gland were collected on the compress. The compress was immediately placed in a flask containing 10 ml of dichloromethane and the flask was agitated several times such that the secretion was deabsorbed.

After obtaining the samples from 10 ducks and 16 chickens 5 ml of solvent (acetonitrile and dichloromethane) was taken from each of the samples of the same series to form a combined sample. The combined sample of 15 ml was then concentrated by ten by evaporating under a stream of air to 1.5 ml.

The sample was then analyzed by gas chromatography/mass spectroscopy (GC/MS) using a Turbo Mass GC/MS from Perkin-Elmer. The column utilized was a JW type DB 5 MS having a length of 30 m a width of 0.25 mm and a film of 0.25 μm. The split used was 1/20 and the split/split less used was 45 seconds. 2.0 μl was injected.

The detection was effectuated on impact using a positive electronic impact (El+) at an energy of 70 eV at 180° C. This technique was used to separate the molecules in a reproducible and characteristic manner.

A data base, known in the art was then interrogated to interpret what molecules in the samples were the closest to the spectra obtained.

To confirm the structure of different molecules, positive Chemical Ionization (CI+) was then performed in methane. This technique is known in the art.

The profiles from the two different chromatographs that were obtained were different from the duck and the chicken. In the chicken a composition of an attractive kairomone as found. In contrast in duck, a repulsive allomone was found as indicated in Table 1 below.

Figure 2:
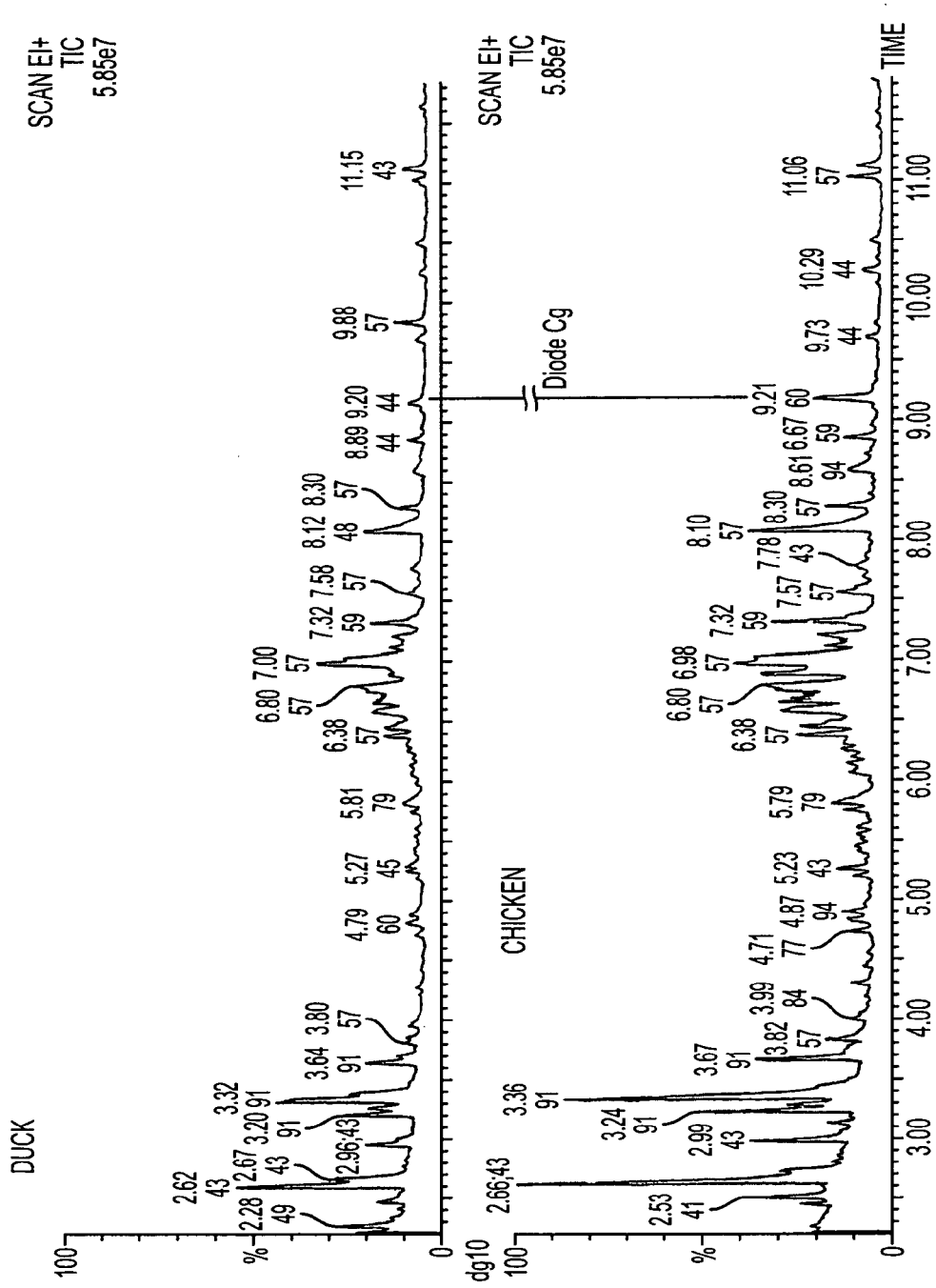
FIG. 2 is another gas chromatography/mass spectroscopy spectrum profile of the components found in the secretions of ducks and chickens from the uropygial gland.
Figure 3:
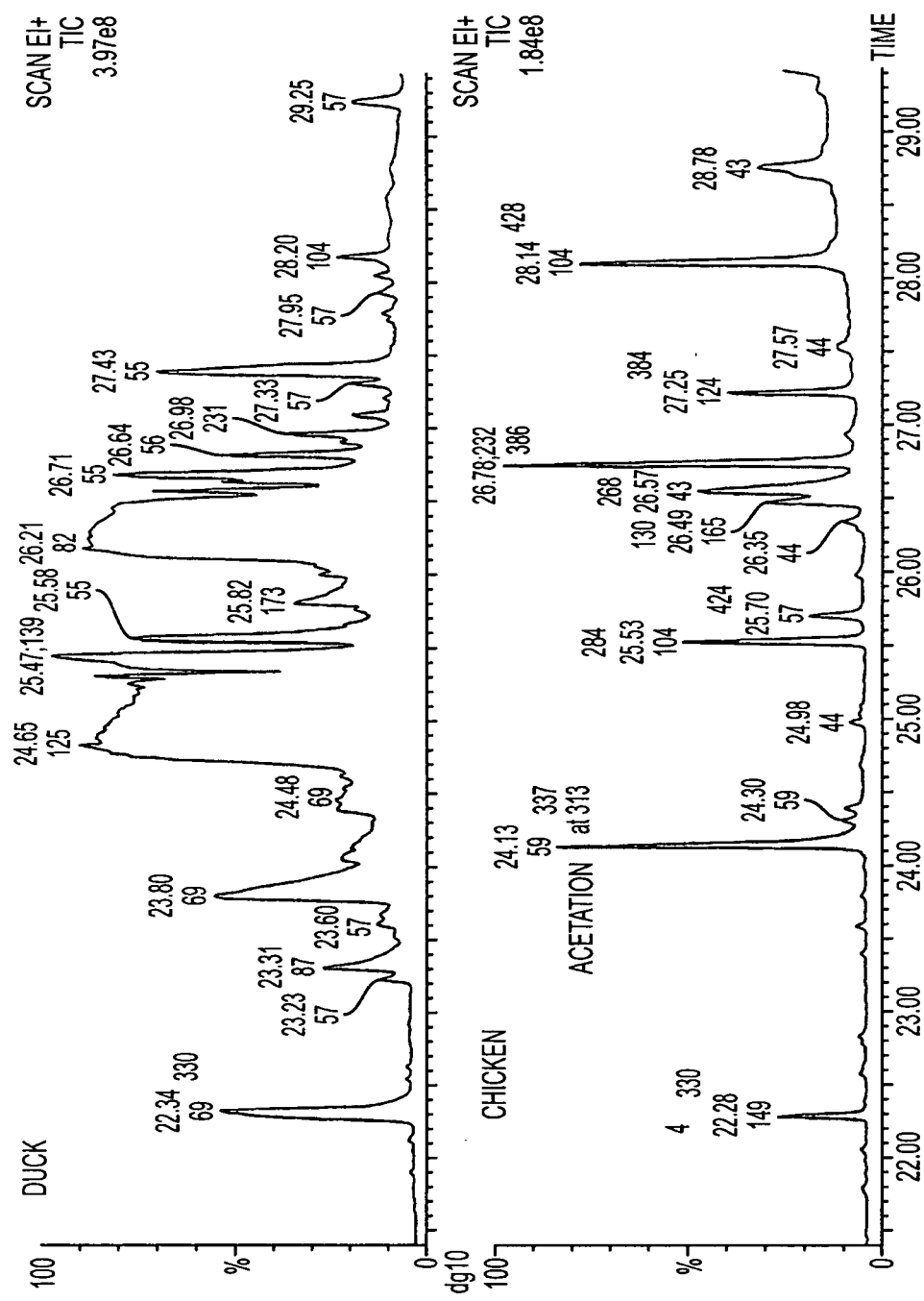
FIG. 3 is yet another gas chromatography/mass spectroscopy spectrum profile of the components found in the secretions of ducks and chickens from the uropygial gland.

The results of the chromatographs are found in FIGS. 1 to 3, for chickens and ducks, respectively.

TABLE 1

| Composition | Application | Molar Mass g/mol | Time of Retention in minutes |
|---|---|---|---|
| 2,2,4-trimethyl 1,3 pentanediol diisobutyrate | Allomone | 286 | 13.37 |
| heptadecene-1-ol | Kairomone | 254 | 17.57 |
| Heptadecane/heptadecene | Kairomone | 240/238 | 17.61 |
| Steroid | Allomone | 284 | 17.80 |
| 9-Octadecene-ol 1 (oleyl alcohol) | Kairomone | 268 | 18.52 |
| Octadecane/octadecene | Kairomone | 254/252 | 18.65 |
| Steroid | Allomone | 312 | 19.60 |
| bis(2-ethylhexyl)adipate | Allomone | 370 | 21.15 |

After complete examination of the chromatographs, the attractive kairomone in chickens was composed of the following composition:

about 23.5 to 26.5 (w %/w %) heptadecene-1 ol about 23.5 to 26.5 (w %/w %) heptadecane/heptadecene about 23.5 to 26.5 (w %/w %) 9-octadecene-ol 1 (oleyl alcohol)

about 23.5 to 26.5 (w %/w %) octadecane/octadecene

After completer examination of the chromatographs, the repulsive allomone from ducks was found to be composed by of the following composition:

about 45.0 to 55.0 (w %/w %) bis(2-ethylhexyl) adipate about 45.0 to 55.0 (w %/w %) 2,2,4-trimethyl-1,3 pentanediol diisobutyrate The specific concentrations of kairomones and allomones as set forth above were used in all of the examples that follow.

Example 2

Selection of Choice of Solvents

The molecules present on the skin are essentially liposoluble and to extract them it is necessary to use an organic solvent. However, organic solvents are extremely irritating to the skin and risk to alter the cutaneous texture, which could induce a modification of behavior in a parasite. Therefore, the following experiments were performed to test different solvents and to identify those which do not alter the cutaneous texture of the skin, as well as being less noxious for the skin as well as the parasite or arachnid.

Four different solvents were tested; namely chloroform, diethyl ether, acetone and 60% ethanol. For each solvent the variation of the amount of feeding *Dermanyssus gallinae* was undertaken for an excised patch of chicken skin washed with the particular solvent and the natural skin.

Each skin was washed three times with 0.5 ml of solvent. In a first group, the skin was washed in vitro and then fed to the arachnids (*Dermanyssus gallinae*). In a second group, 0.5 ml aliquot of solvent was placed on the already washed skin and was permitted to evaporate. In a third group, the skin was washed in a liquid obtained after washing a different chicken or duck skin. For 60% ethanol, after washing and letting this solvent evaporate, the skin was again washed twice with 0.5 ml water.

Figure 4:
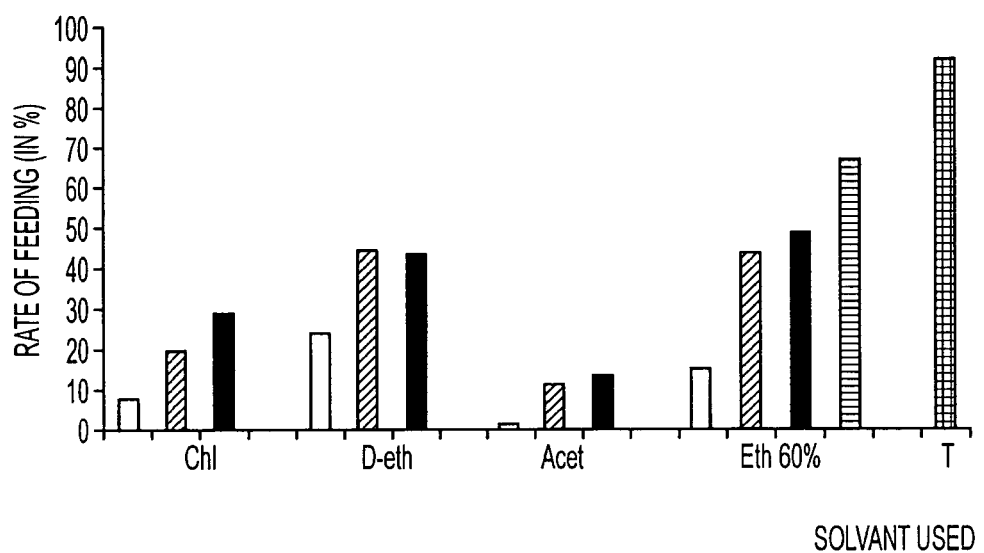
FIG. 4 is a graph demonstrating the types of solvents used. Ch1 stands for chloroform, D-eth stands for diethyl ether, Acet stands for acetone and Eth 60% stands for 60% ethanol. ☐ means the level of feeding of mites with skin washed with the solvent, ■ stands for the level of feeding of mites after depositing on the skin a product washed with the another skin, ☐ stands for the level of feeding of mites after depositing on the washed skin a product that was washed and rinsed with water and ☐ means level of feeding of mites for the natural skin of chicken.

The results are set forth in FIG. 4. It is clear from this Figure that 60% ethanol should be used as the solvent since there is on the sebaceous layer of the chicken skin one or more substances that attract the feeding of *Dermanyssus gallinae*.

Example 3

Tests with the Extracts

The skin of chickens and ducks was utilized in this example to search for the presence of kairomones and allomones in these two different birds. The skin of the ducks and chickens were washed with 0.5 ml 60% ethanol three times and the aliquots from these washings were collected. 0.5 ml of the washing aliquots were then redeposited on the same skin another three times and an one hour period was maintained between each washing to permit the alcohol to evaporate. After the three last washing, the skin was washed once with 0.5 ml of deionized water.

Extracts from the uropygial gland or tail gland were deposited on the chicken skin or duck skin washed with ethanol. These extracts were diluted 1/20 prior to being deposited. This dilution takes into account the volume of the raw secretion that was found settled throughout the entire body.

Figure 5:
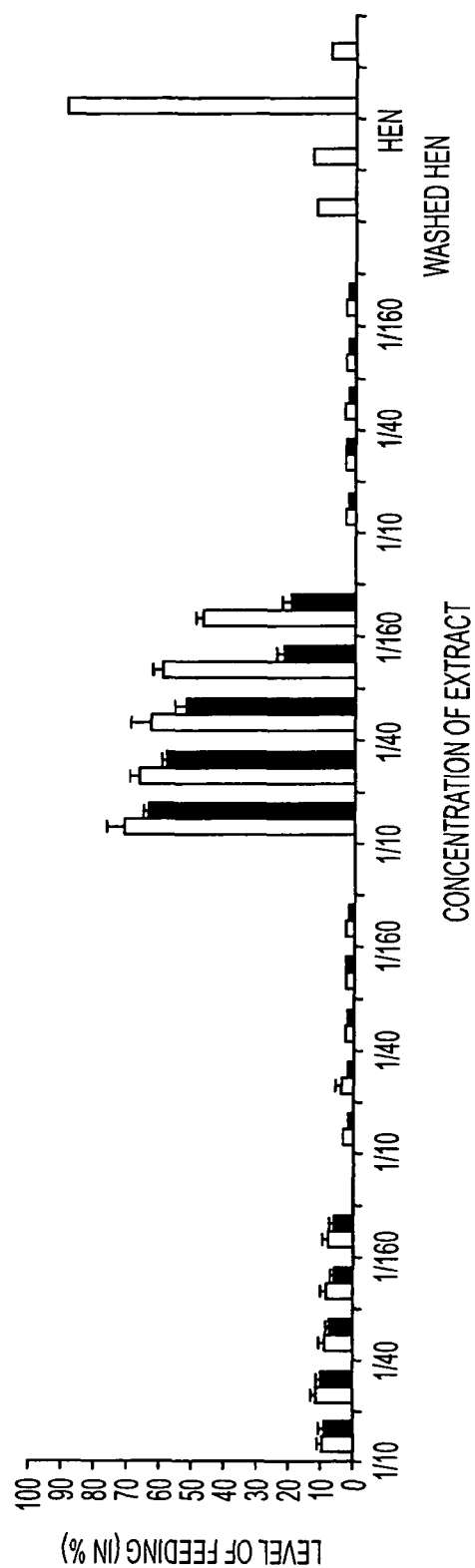
FIG. 5 is a graph showing the percent of feeding of *Dermanyssus gallinae* with various concentrations of extracts derived from the chicken or duck uropygial gland with different concentrations of extract diluted with solubilized alcohol using a 1/10 to 1/160 dilutions. The first group of extracts was tested with washed chicken skin. The second group of extracts was tested with washed duck skin. The third group of extracts was tested with unwashed chicken skin and the fourth group of extracts was tested with unwashed duck skin. These extracts were from the duck uropygial gland; one was solubilized in alcohol (☐) and the other in acetonitrile (■).

*Dermanyssus gallinae* (30 per tube) were applied to either the chicken skin or the duck skin. Three tubes were used in this experiment, each containing 30 *Dermanyssus gallinae*. The results are set forth in FIG. 5. From these experiments it was concluded that there exists on the skin one or more substances that potentiates the feeding of the Arcadnida and is a kairomone. This kairomone is present in the uropygial or tail gland. There also exists on the skin of a duck one or more substances that have a repulsive effect on the Arcadnida and are also found in the uropygial or tail gland. These substances are allomones.

Figure 6:
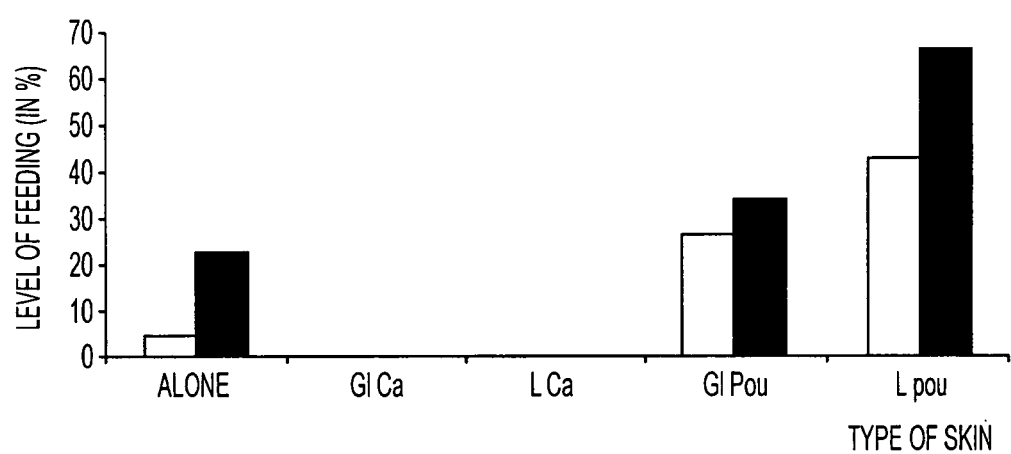
FIG. 6 is a graph illustrating the percent of feeding of *Dermanyssus gallinae* with extracts of uropygial gland from the duck (☐) or from chicken (■). Alone stands for feeding of the mites on washed skin; GL Ca stands for feeding of the mites with washed skin plus the extract from the uropygial glands from duck; LCa stands for the feeding of the mites from washed skin plus the product of washings from the duck. Gl Pou stands for feeding of the mites on skin washed plus the extract from the uropygial gland of chicken. Lpou stands for stands for the feeding of the mites from washed skin plus the product of washings from the chicken.

Extracts of the uropygial gland of the duck and chicken were diluted 1/10, 1/20, 1/40, 1/80, and 1/160 with ethyl alcohol. Four pieces of absorbent papers were placed in a Petri dish. On one of the papers a known miticide was placed (LD 100 in 12 hours at 1.20 of the dose prescribed.) On the other paper the products of extraction were placed. The mites were introduced into the Petri dish. The Petri dish was closed and placed in a dry area for 12 hours. After 12 hours the dead mites were counted. The results are shown for the extracts in FIG. 6.

Example 4

Testing of the Repulsive Allomone in Young Chicks

A cage was infested with *Dermanyssus gallinae* at a level of infestation of 5/8. The maximum observed in breeding is 6/8. This means around 60 mites per $cm^2$.

The cage was separated into two compartments. One compartment contained only the feedstuff. This separation permitted a free circulation of the mites between both compartments but not the young chicks, which were restricted to the compartment that did not contain the feedstuff. The two zones of the cage were equally infected with the chicken mites. The young chicks used in this example were a day old.

The chicks were separated into two lots. Lot A was fed with a feedstuff supplemented with Duck Repulsive Allomone (hereinafter DRA) and lot B with regular feedstuff at Day 1. 800 µg/200 g of DRA, thus 4 mg/kg was added to the feedstuff.

The quantity of feedstuff eaten was for the chicks on the average from 15 g to 20 g.

Four chicks in each were introduced into the cage with two compartments. All dead chicks were immediately taken out and replaced to maintain 4 animals in each compartment. The experiment took place over 11 days. The following results are shown in Table 2 below.

TABLE 2

| Day | Number of Deaths Lot A | Number of Deaths Lot B |
|---|---|---|
| 0 | 0 | 0 |
| 1 | 4 | 4 |
| 2 | 4 | 4 |
| 3 | 3 | 4 |
| 4 | 0 | 2 |
| 5 | 0 | 3 |
| 6 | 0 | 1 |
| 7 | 0 | 1 |
| 8 | 0 | 1 |
| 9 | 0 | 0 |
| 10 | 0 | 0 |
| 11 | 0 | 0 |
| Total Deaths | 11 | 20 |

The above results prove the efficacy of protection of DRA in foodstuff for chicks against chicken mites.

Example 5

Testing of the Repulsive Allomone in Broiler Hens and Chickens

Different concentrations of Duck Repulsive Allomone (hereinafter DRA) were tested in foods of broiler hens and chickens of the industrial type at a base concentration of 200 µg feedstuff/animal/day according to Table 3 set forth below:

TABLE 3

|  | Group 1 | Group 2 | Group 3 | Group 4 |
|---|---|---|---|---|
| Dose DRA in µg/animal/day | 0 | 32 | 160 | 800 |
| Treatment | A1 | A2 | A3 | A4 |

Figure 7:
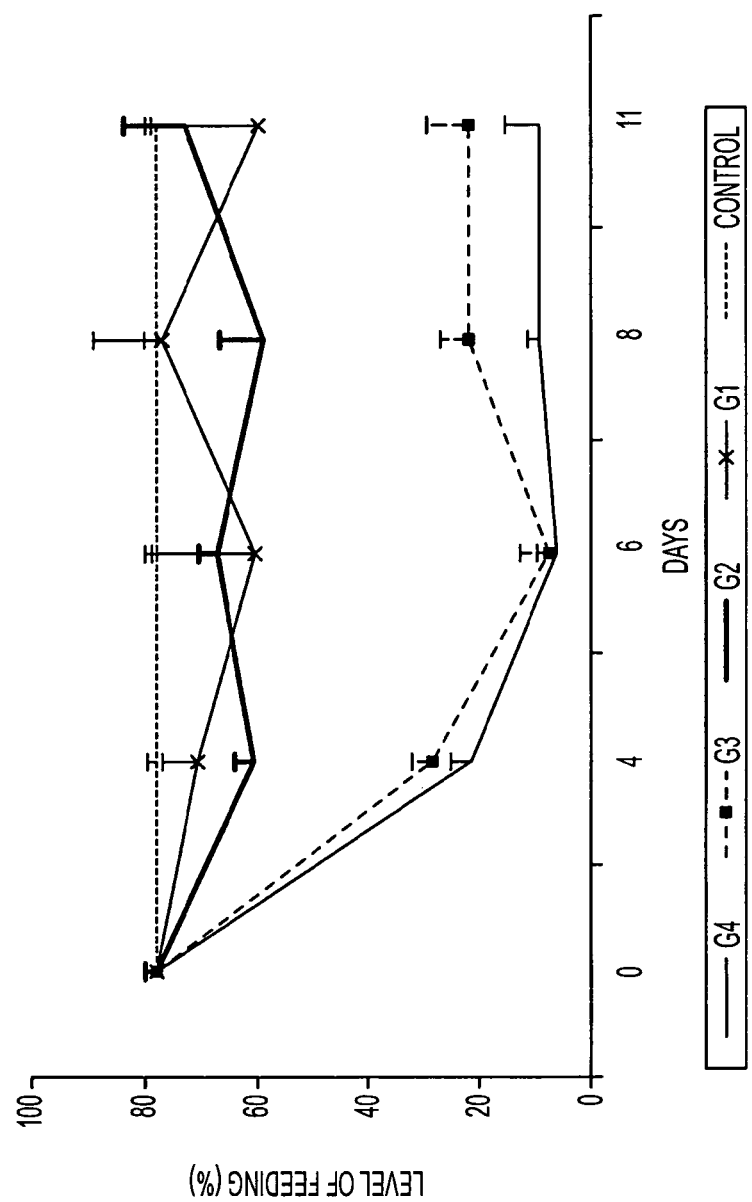
FIG. 7 is a graph showing the feeding percentage of *Dermanyssus gallinae* over a period of 11 days after hens were given the duck repulsive allomone of the present invention in the feedstuff.
Figure 8:
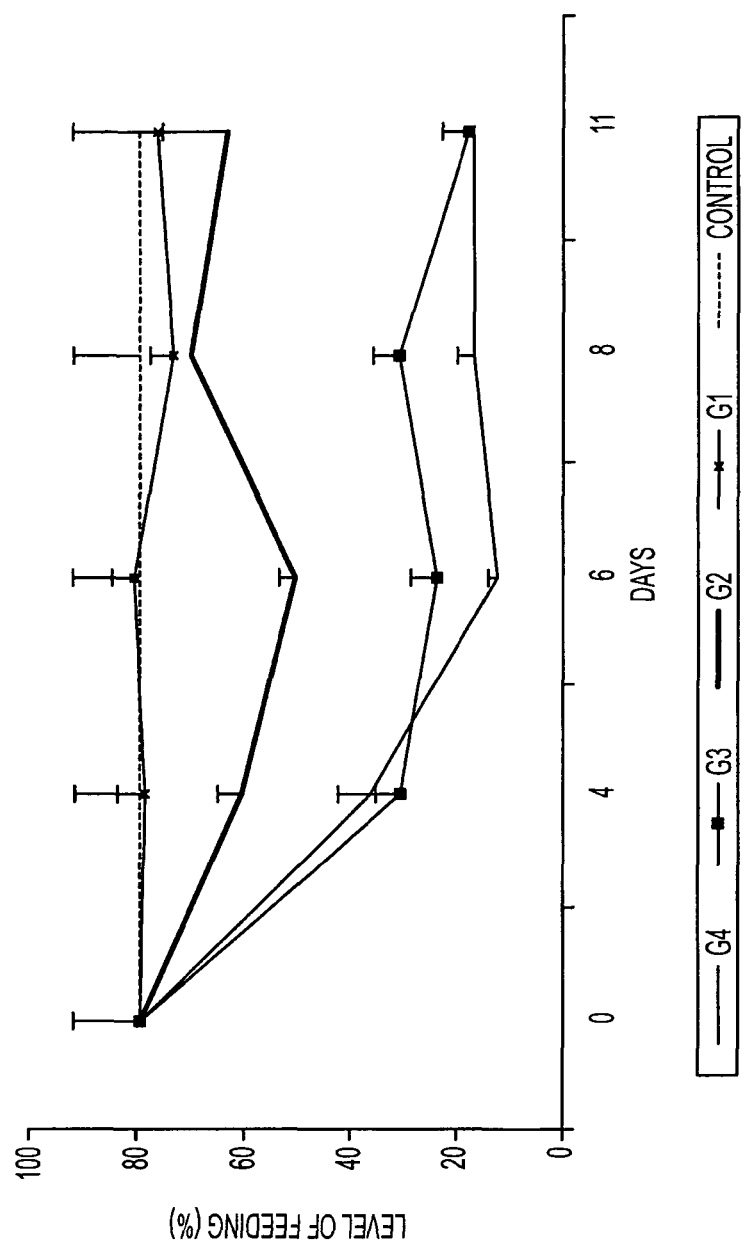
FIG. 8 is a graph showing the feeding percentage of *Dermanyssus gallinae* over a period of 11 days after chickens were given the duck repulsive allomone of the present invention in the feedstuff.

The results obtained are shown in FIGS. 7 and 8.

These results show that two concentrations protect the hens against the attack of *Dermanyssus gallinae* since the level of feeding is inferior to 20% and this is the acceptable limit tolerated in chicken in stock farming. The comparison with the other concentration and the control show that the variation is significant. In effect, Group 3 and Group 4 had a level of feeding inferior to the three other groups (Control Group 1 and Group 2). Therefore there exists an effective dose of the DRA integrated in the feedstuff.

The small inflexion of the curves for Group 3 and Group 4 at day 8 was a variation in the protocol since these groups of animals were not fed ad libitu during the day prior to this experiment.

The curves in FIGS. 7 and 8 show that the results are identical between the hen and the chicken and therefore the DRA does not have a different effect on the different sexes.

The statistical differences using the test permit to compare the different groups with the control and the show the statistical differences, which are as follows:

(1) $p<0.0001$ to $p<0.005$ the maximum for Group 4 vs. control at day 4.

(2) There exists a significant difference between Group 3 and Group 4 for day 6 (chickens) day (hens and chickens) and day 11 (hens): $p<0.01$ for each of these comparisons.

(3) For Group 4, the variation was significantly different from the other three groups: $p<0.0001$ for Group 4 vs. control, Group 1 and Group 2.

Example 6

Testing the Allomone with Neutral Blood and DRA

Figure 9:
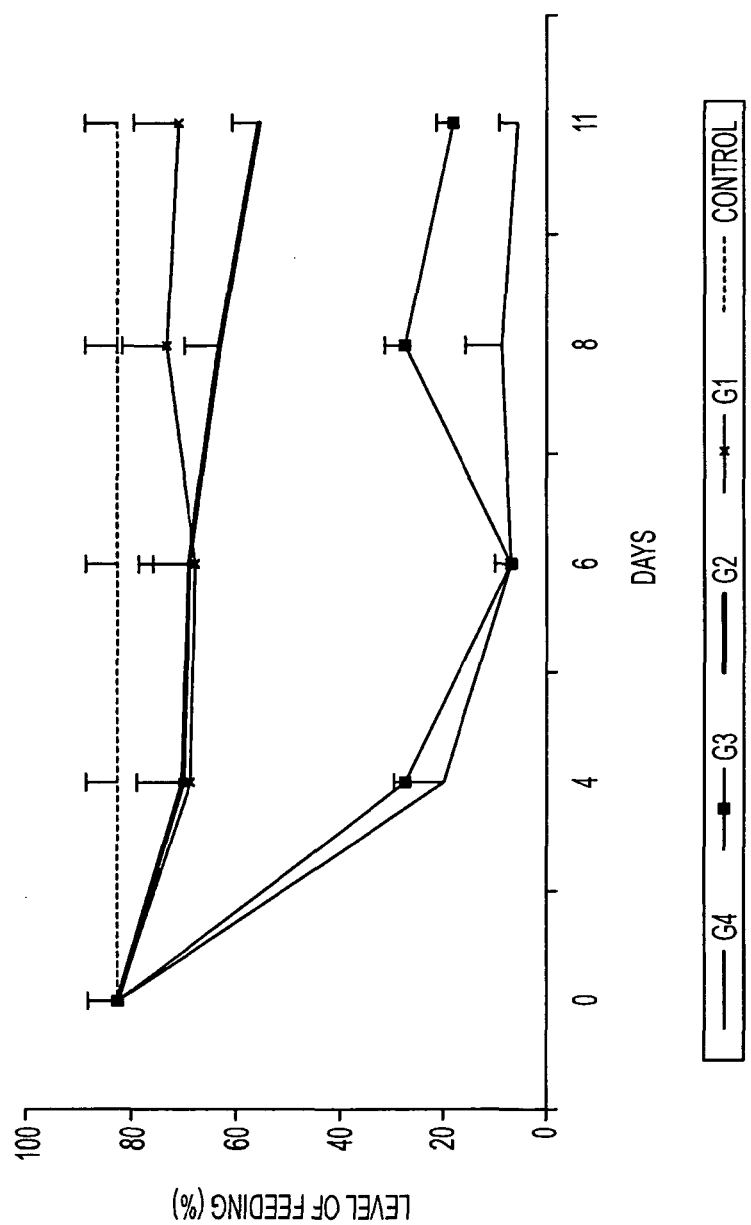
FIG. 9 is a graph showing the feeding percentage of *Dermanyssus gallinae* over a period of 11 days after the hens were given the duck repulsive allomone of the present invention in the feedstuff and neutral blood. By "neutral blood" is meant the blood of a chicken that has been fed with normal food.

In this experiment neutral blood was used and the hens and chickens skin was supplemented with the DRA ($p<0.0007$) and the same groups and treatment were used as in Example 4 (see Table). The mites fed at the same level as previously in Example 5. The results are shown in FIG. 9.

There were significant differences between Group 1 and Group 2 and the control. One notes the similarity of the two graphs with significant variations between Group 3 and Group 4 for day 8 and day 11.

Example 7

Testing of the Allomone in the Blood

Figure 10:
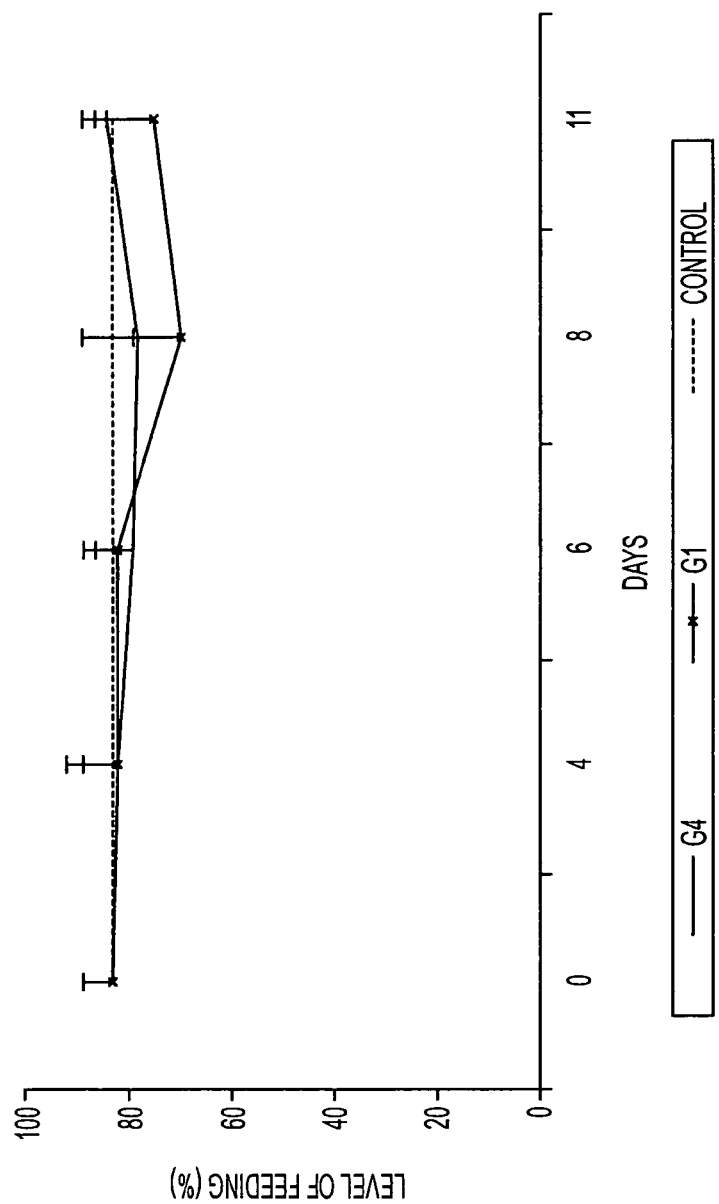
FIG. 10 is a graph illustrating the feeding percentage of *Dertpanyssus gallinae* over a period of 11 days using the blood of hens supplemented with the duck repulsive allomone of the present invention.

FIG. 10 confirms that the DRA does not enter into the blood of the animals tested. This test was effectuated using a blood index of *Dermanyssus gallinae*. Also the substances ingested with the feedstuff could be absorbed in the course of digestion. The use of neutral skin with the blood of the animal supplemented with DRA permits to demonstrate that the DRA was found on the skin and thus excreted from the animal cutaneously.

The mites were induced to feed through a piece of normal skin, but the proposed blood was a sample of blood obtained from chickens fed with DRA.

Example 8

In this example the Duck Repulsive Allomone (hereinafter DRA) was incorporated into the feedstuff and in the water and compared with a neutral control and a placebo group. 200 ml of DRA was placed in the water/animal/day and 200 µg of DRA was put into feed/animal/day. The following Table 4 illustrates the groups and their dosages in this Example. The chicken consumed on the average about 120 g to 150 g of feed.

TABLE 4

|  | Group 1 | Group 2 | Group 3 | Group 4 | Group 5 | Group 6 |
|---|---|---|---|---|---|---|
| Dose DRA in µg/animal/day |  |  | 00 |  | 60 | 00 |
| Water | Neutral | Neutral | Neutral | Water 1 | Water 2 | Water 3 |
| Feed | Neutral | Feed 1 | Feed 2 | Neutral | Neutral | Neutral |

Figure 11:
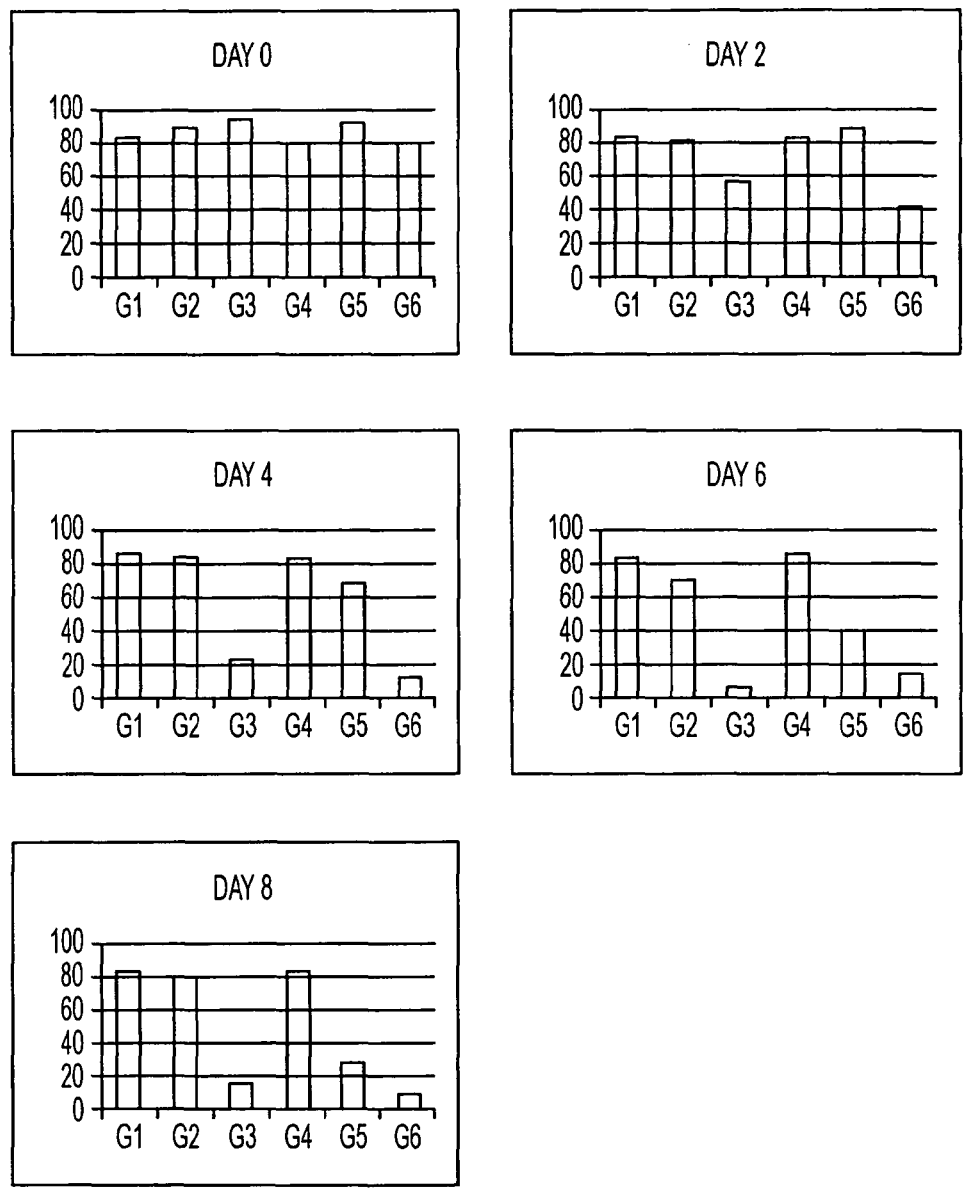
FIG. 11 are various graphs at different days illustrating the feeding percentage of *Dermanyssus gallinae* with six different groups tested with either a placebo or the duck repulsive allomone of the present invention placed in either water or in the feedstuff from day 0 to day 6.
Figure 12:
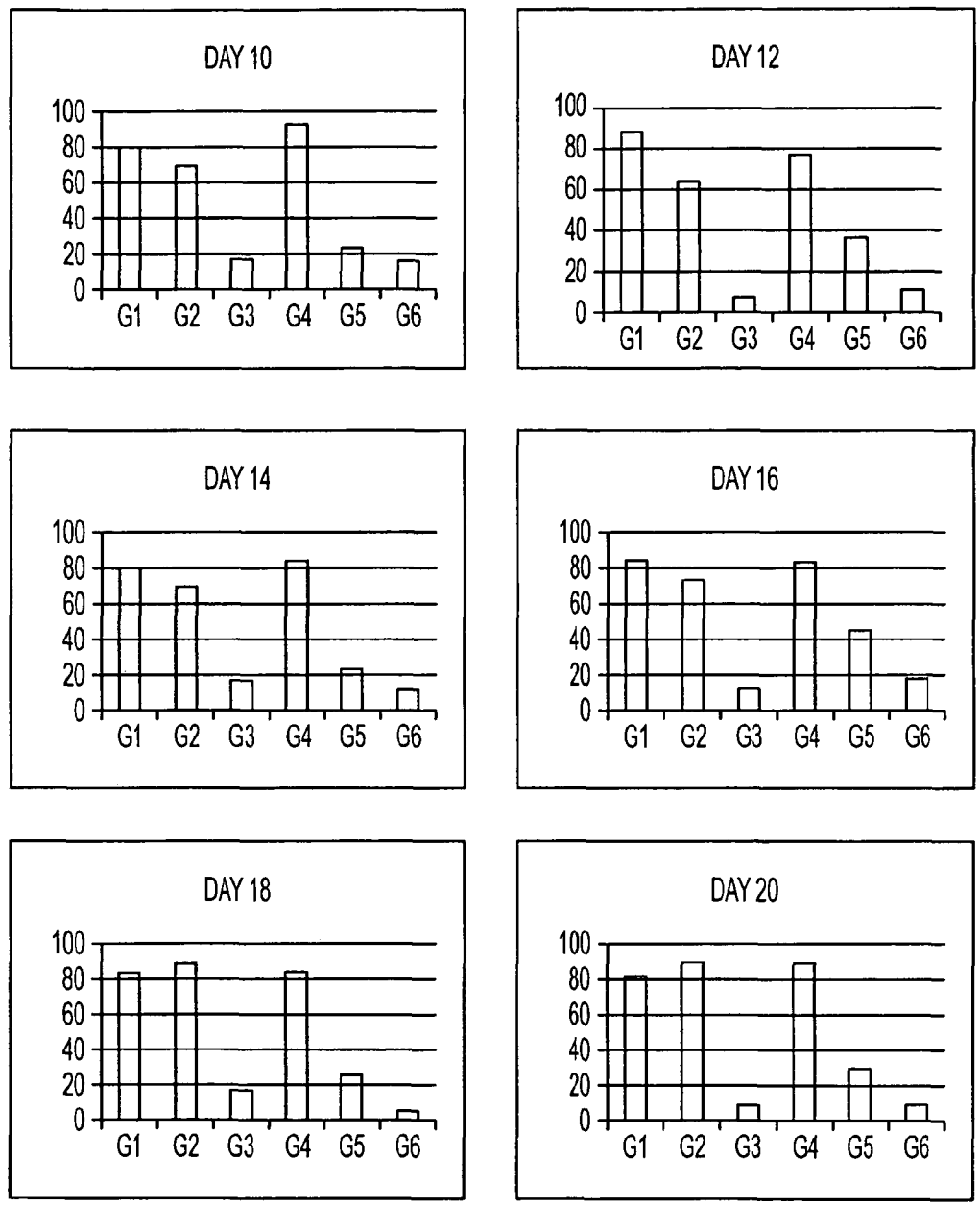
FIG. 12 are various graphs at different days illustrating the feeding percentage of *Dermanyssus gallinae* with six different groups tested with either a placebo or the duck repulsive allomone of the present invention placed in either water or in the feedstuff from day 10 to day 20.

Also, Groups 2 and 4 constitute the placebos while Group 1 is the control. FIGS. 11 and 12 at day 0 to day 20 indicate the results in terms of feeding until the slaughtering of the chickens.

FIG. 11 indicates the significant differences between the control group and the placebo group starting at day 4 for Group 3 for all of the tests ($p<0.0001$ at day 4 and $p=0.0025$ at day 20 compared to Group 1. For Group 1 versus Group 6, $p=0.015$ at day 2, $p<0.0001$ at day 4 and $p=0.0031$ at day 20). The differences for these 2 groups is very significant for all of the tests.

Therefore the differences between Group 1, group 2 and Group 4 are significantly important. One notes a decrease in the level of feeding in the chicken mites when DRA is used.

There was no variation between groups 3 and 6 that demonstrates a perfectly linear kinetics of non-feeding. The variation is noted for the four other groups. Also the level of feeding statistically diminished between day 8 and day 10

(day 10 being equivalent to day 12) for the placebo group which was different than the control. The variation for Group 5 was noteworthy.

There was no notable difference between the two modes of administration (water vs. feedstuff) in an average dose as reflected in Groups 3 and 6, which provided good protection to the animals.

Example 9

Allomone Protection in Young Chicks and Hens

This example illustrates the time of apparition of protection with young chicks in comparison with hens. The procedure was the same as that in Example 4; i.e., the DRA was added to the feedstuff.

The hens consumed on the average about 120 g to 150 g of feedstuff, while the young chicks consumed on the average about 15 g to 20 g of feedstuff.

It should be noted that the young chick does not produce a cutaneous film before a certain age and thus the treatment may have a different effect than that on adult hens and chickens.

The results at day 6 are set forth in the following Table 5.

TABLE 5

| Group | Feeding % | Standard Deviation (%) | P Value |
|---|---|---|---|
| DRA | 5.6 | 5.1 | <0.0001 |
| Placebo | 93.3 | 3.3 | |

As can be seen from the above Table 5, the feeding was quite diminished as compared to the placebo group on day 6. The p values were all p<0.0001 just until day 20 when the p value was 0.003. At day 14 it was decided to stop the treatment with DRA and return to regular feedstuff, in order to observe the kinetics of disappearance and the effect of protection of DRA. On day 16 the following augmentation of feeding was observed as set forth in the following Table 6.

TABLE 6

| Comparison | Feeding (5) | Standard Deviation (%) | P Value |
|---|---|---|---|
| Day 14 vs. Day 16 | 2.2 vs. 15.6 | 3.8 vs. 5.1 | 0.022 |
| Day 14 vs. Day 18 | 2.2 vs. 8.9 | 3.8 vs. 3.9 | 0.101 |
| Day 14 vs. Day 20 | 2.2 vs. 35.6 | 3.8 vs. 8.4 | 0.003 |
| Day 14 vs. Day 22 | 2.2 vs. 24.4 | 3.8 vs. 6.9 | 0.008 |
| Day 14 vs. Day 24 | 2.2 vs. 26.7 | 3.8 vs. 12.0 | 0.028 |
| Day 14 vs. Day 26 | 2.2 vs. 26.7 | 3.8 vs. 6.7 | 0.053 |
| Day 14 vs. Day 28 | 2.2 vs. 51.1 | 3.8 vs. 5.1 | <0.001 |
| Day 14 vs. Day 30 | 2.2 vs. 66.7 | 3.8 vs. 3.3 | 0.003 |

The results in the above Table 6 prove that the young chicks are only protected after treatment with DRA for a period between 0 to 48 hours after the end of treatment with DRA. Therefore, it is necessary to continually treat young chicks for the duration of their growth.

However, it should be noted that the difference between the placebo and those chicks treated with DRA is significant at day 28 (p=0.006) and thus the protection still existed at day 28.

Figure 13:
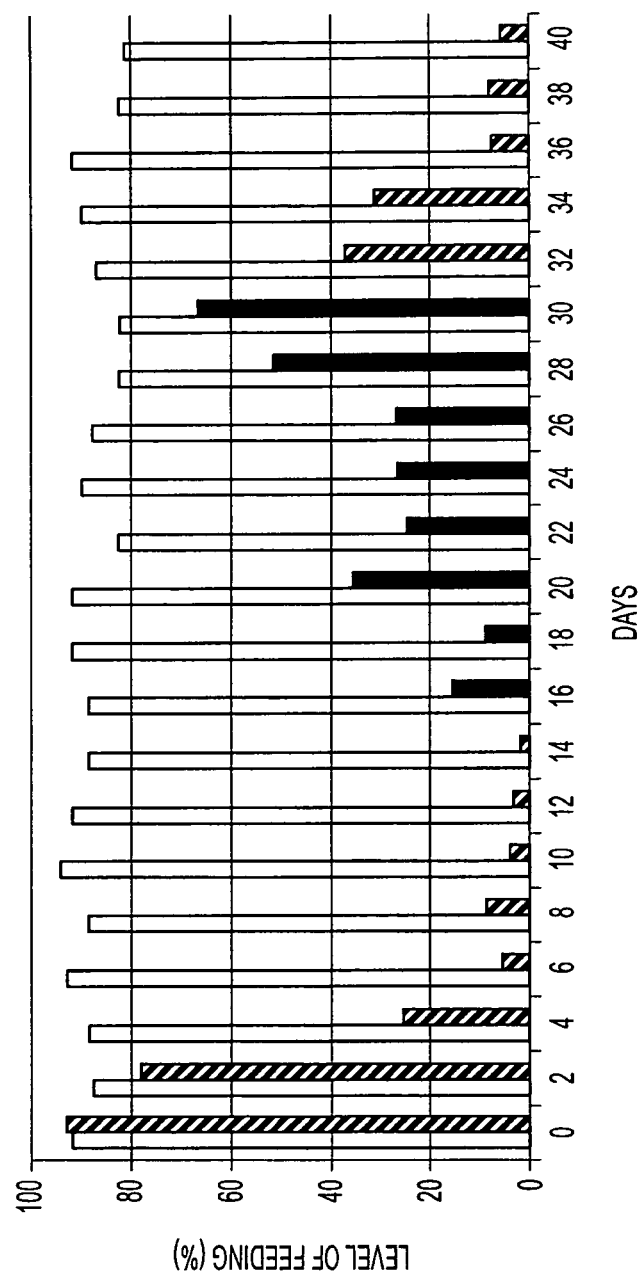
FIG. 13 is a graph at different days illustrating the feeding percentage of *Dermanyssus gallinae* on young chicks. ☐ stands for the control; ■ stands for administration of the duck repulsive allomone in the feedstuff which was stopped; ▤ stands for administering the duck repulsive allomone of the invention to the young chicks.
Figure 14:
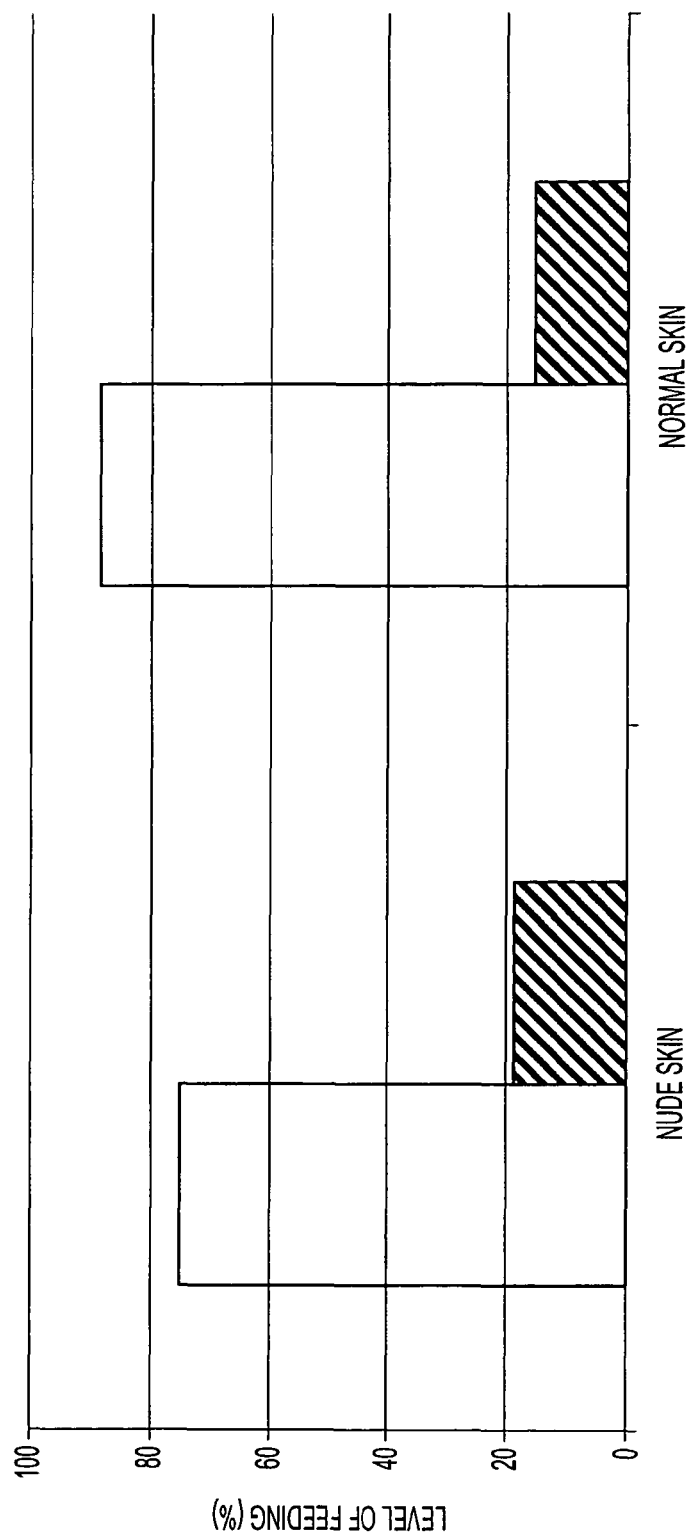
FIG. 14 is a graph illustrating the feeding percentage of *Dermanyssus gallinae* on normal chicken skin with feather and nude chicken skin without feathers. ☐ stands for the control; ▤ stands for administering the duck repulsive allomone of the invention.
Figure 15:
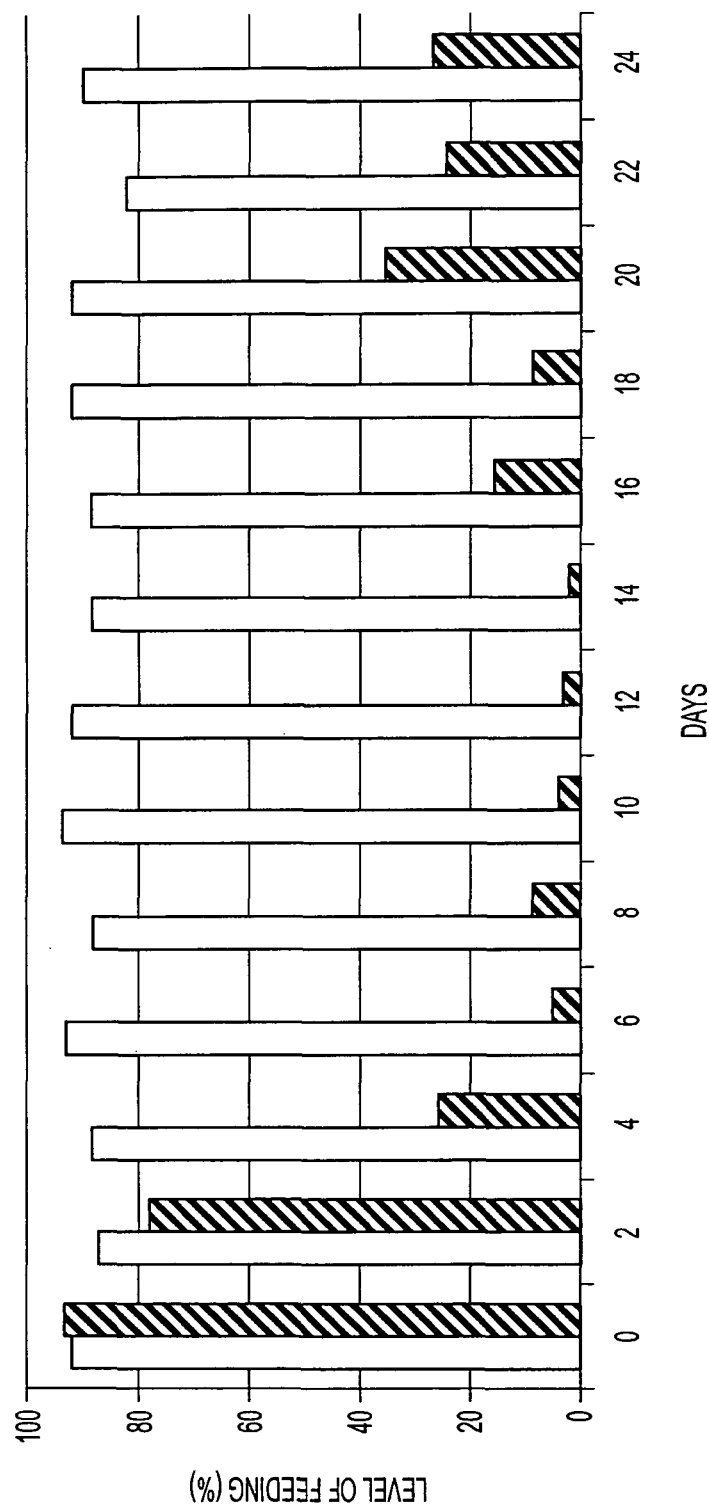
FIG. 15 is a graph illustrating the feeding percentage of *Dermanyssus gallinae* on young chicks over a period of twenty-four days. ☐ stands for the control; ▤ stands for administering the duck repulsive allomone of the invention.

At day 30 the young chicks were placed back on treatment. FIGS. 13 and 15 illustrate that the effect of protection with DRA is much less at day 30 than 14 days after the end of the treatment with DRA (p=0.011 for DRA vs. placebo). The reappearance of the protecting effect is, however, almost immediate (p=0.0008 at day 32), if one considers that the DRA has disappeared.

Thus, once the DRA treatment has been stopped, the mites recovered their feeding behavior. Immediately after readministering the treatment one observes the repulsive effect. Therefore for protection it is better to maintain the special diet with DRA.

Example 10

Use of Different Skin Types

In this Example, two (2) different types of skin were treated with DRA; i.e., nude skin and skin with feathers. The skins that were treated were those of chickens fed with normal food or with DRA. Half of the skin feathers were removed and half the skin feathers were maintained.

The nude skin had less *Dermanyssus galinae* (p=0.033 for placebo vs. placebo). It appeared that feathers have a certain type of attraction to *Dermanyssus gallinae*. However, the difference between the placebo and the skin treated with DRA was significant (p<0.0001 for placebo vs. DRA). Thus it appears that the chemical signals seem to be "concentrated" on the feathers.

Example 11

A solution of about 23.5 to 26.5 (w %/w %) heptadecene-1, about 23.5 to 26.5 (w %/w %) heptadecane, about 23.5 to 26.5 (w %/w %) 9-octadecane-ol 1 (oleyl alcohol) and about 23.5 to 26.5 (w %/w %) octadecane is made.

The interior of container made of plastic and having openings is saturated with a polyacrylate adhesive material in order to entrap mites. The kairomone solution is then added to the interior of the container which is then placed in a hen house. The mites which are baited with the kairomone solution are then entrapped in the container after a few days. The container is then disposed of.

Example 12

The same container with the kairomone as in Example 11 is used in this example. The container was placed in a window well outside of a house where numerous black widow spiders were nesting. The black widow spiders which are baited with the kairomone solution are then entrapped in the container after a few days.

The container is then disposed of.

Example 13

A dog is washed with a shampoo comprising about 45.0 to 55.0 (w %/w %) bis(2-ethylhexyl) adipate and about 45.0 to 55.0 (w %/w %) 2,2,4-trimethyl-1,3 pentanediol diisobutyrate. The dog is later walked through a woods that is generally infested with ticks. The dog is later searched for ticks and none were found since the allomone in the shampoo repulsed this arachnid.

Example 14

The same method is applied as in Example 13, but cats are used. The cat is later searched for ticks and none were found since the allomone in the shampoo repulsed this arachnid.

Example 15

A child is washed with a shampoo/soap comprising about 45.0 to 55.0 (w %/w %) bis(2-ethylhexyl) adipate and about 45.0 to 55.0 (w %/w %) 2,2,4-trimethyl-1,3 pentanediol diisobutyrate. The child is later walked through a woods that is generally infested with ticks. The child is later searched for ticks and none were found since the allomone in the shampoo/soap repulsed this arachnid.

Example 16

A chicken breeder is washed with a soap comprising about 45.0 to 55.0 (w %/w %) bis(2-ethylhexyl) adipate and about 45.0 to 55.0 (w %/w %) 2,2,4-trimethyl-1,3 pentanediol diisobutyrate. The chicken breeder enters the hen house and works with the chickens, hens and young chicks most of the day. The chicken breeder notices that less mite bites are on the body than without washing with the soap.

Example 17

This example illustrates the efficacy of the Duck Repulsive Allomone (DRA) when given in the drinking water of egg laying hens suffering from a chronic and massive parasitic infection by *Dermanyssus gallinae*.

The hen house was first visited by the persons involved in the study and an initial inspection was undertaken of the hen house infected with *Dermanyssus gallinae* with the head aviculturist of the hen house being present. The hen house was inspected by the investigators wearing boots and gloves. The hens were then divided into 7 rows in the hen house and each row was assigned a number of 1 to 7.

The head aviculturist was requested to choose two hens randomly from each of the seven rows of hens. Blood was taken from each of the randomly chosen hens and an autopsy of the hens was also performed. 4 mls of blood was taken from the alar vein of each hen. Part of the blood was placed in a test tube that did not contain any chemical additives and the other part was placed in a test tube containing EDTA. The blood samples were then placed in an isothermic recipient that had refrigerating blocks. They were analyzed the next day in a laboratory.

After the blood sampling, the randomly chosen hens were sacrificed and subjected to a complete autopsy, including a search for external parasites. During the autopsy a trace of the mucosa Caecal from the wall of the Caecal was taken and placed in 10% formalin to eventually search for infestations by protozoa.

At the time that the investigators were in the hen house, an in-depth exam was made of the hen house by collecting and counting the number of arachnids present. Each row in the hen house had 60 cages of hens on each level and there were three levels. Visible arachnid colonies and dust was collected for 20 cages. Each of the specimens was placed in air-tight jars and taken to a laboratory to determine the identity and the number of arachnids present. The colonies of arachnids were counted for 12 cages and the largest diameter of the arachnids' colonies was measured for each of the 12 cages. Finally, the sampling of 15 milliliters of droppings for each row was undertaken underneath each row, which accounted for all of the droppings of the hens for the three levels.

Also during this visit the investigators showed the chief aviculturists how to use the product called P1 which was 50% (w %/w %) of bis(2-ethylhexyl) adipate and 50% (w %/w %) 2,2,4 trimethyl 1,3 pentanediol diisobutyrate and a specific protocol of administration of the product was given to him. The treatment began after the first visit (V1).

The Products Utilized in the Treatment

Three products having different analogues of DRA, representing the active principal, were used and placed into an aqueous solution. The solutions did not vary by their nature, but only with respect to the tensioactives and conservatives used. The following solutions were utilized in the treatment:

Solution 1: a titrated 4% (w %/w %) solution of DRA 50% (w %/w %) of bis(2-ethylhexyl) adipate and 50% (w %/w %) 2,2,4 trimethyl 1,3 pentanediol diisobutyrate) and brought to 100 ml. with ethanol. This product was placed in water bottles of 2.5 liters.

Solution 2: a titrated 4% (w %/w %) of DRA 50% (w %/w %) of bis(2-ethylhexyl) adipate and 50% (w %/w %) 2,2,4 trimethyl 1,3 pentanediol diisobutyrate) containing 5% (w %/w %) of polysorbate 80 and brought to 100 ml using ethanol. This product was placed in water bottles of 5 liters.

Solution 3: a titrated 4% (w %/w %) of DRA 50% (w %/w %) of bis(2-ethylhexyl) adipate and 50% (w %/w %) 2,2,4 trimethyl 1,3 pentanediol diisobutyrate) containing 5% (w %/w %) of polysorbate 80 and brought to 100 ml using water. This product was placed in water bottles of 4 liters.

The first solution 1 was presented to the aviculturist at V1. A control was performed by using lots of two successive generations of the DRA product. Telephonic interviews with the aviculturist were undertaken to discuss problems associated with administering the DRA products with the investigators.

In the course of one of the telephonic interviews, it was decided to evaluate the formulation of the product.

Administration of the Treatment

The product was administered in water bottles. The very feeble miscibility of solution 1 in water required the atomization in each water bottle by the reservoir in each row of hens. Solution 1 was placed in the water bottle with a syringe of 50 ml and each dose was then atomized in the reservoir by passage through a needle possessing an exterior diameter of 0.5 millimeters. This operation was performed morning and night.

Duration of Treatment

The treatment was consumed during a period of these 32 days. During the first 10 days, the first solution was used as the treatment. The following 6 days, the second solution was administered as the treatment and in the 16 remaining days, solution 3 was administered as the treatment.

The amount of product consumed during this 32 day treatment is set forth in the following Table 7:

TABLE 7

|  | Quantity Given (liters) | Quantity that rested (liters) | Quantity Consumed (liters) | Theoretical Quantity consumed (liters) | Rate Observed (%) |
| --- | --- | --- | --- | --- | --- |
| Solution 1 | 10 | 2.5 | 7.5 | 7 | 93% |
| Solution 2 | 15 | 8.4 | 6.6 | 4.2 | 63% |
| Solution 3 | 16 | 4 | 12 | 8.9 | 74% |

The rate observed for the calculation of solutions 2 and 3 can be explained by the method of administration of these two solutions. To facilitate the manipulation of these solutions the aviculturist placed a variable amount of these products (solutions 2 and 3) in a very small volume of a salad bowl prior to aspirating the dose which was administered. Thus, due to this variation a theoretical quantity which was consumed was therefore calculated.

No other treatment for arachnids was given during the 32 days in which the hens were treated.

A second visit (V2) to the hen house was undertaken after the 32nd day treatment. As in visit 1, the head aviculturist was requested to choose two hens randomly from each of the seven rows of hens and blood and an autopsy was performed using the same procedure as visit 1 with the exception that the copies of Caecel were not taken from the hens that were autopsied. This exception was due to the finding of an absence of parasites after the evaluation of the samples of the group 1 visit. The autopsy results from visit 1 in the different hens indicated that macroscopic anomalies existed in different organs, so that diverse collections were taken for autopsy for an histopathic analysis. The uropygial glands were also removed in the autopsy of visit 2 to determine whether the DRA was present in the secretions.

Samples were also taken from each of the different reservoirs of water in which the treatment was placed. The samples were then analyzed in a laboratory to ascertain whether the chemical composition of the DRA product was altered or not.

The observations maintained by the aviculturist during the experiment were recuperated.

Criteria Used for the Evaluation

The efficacy of the product was evaluated using three parameters: parasitological parameters, medical parameters and zootechnical parameters.

Parasitological Parameters

All of the arachnid population was regrouped and tests were performed to evaluate the vigor of the arachnids, the number of arachnids and the amount of infestation in different zones of the hen house. In vitro tests were performed to measure the amount of inhibition of feeding of the arachnids in the presence of the DRA in the uropygial gland secretions of the autopsied hens and the droppings obtained in visit 2. For each category of the parasitological parameters that were measured, the results for each row were calculated separately. A comparison of the total parasites was compared before and after treatment, which results were also compared to those performed in the laboratory.

The behavior of feeding of the arachnids in a test tube and in a cage with a host (chick) was observed, as well as the social behavior of the arachnids under the same conditions. An analysis of the cuticles of the arachnids by GC/MS was also performed.

Medical Parameters

The infestation by *Dermanyssus* presents hematological problems with the hens that are infested. This is why blood was drawn at visit 1 and visit 2 of 14 hens that were randomly chosen. The following analysis was then performed on the blood samples:

(1) Hematocrit;
(2) Blood count which permits to evaluate the leucocyte/lymphocyte ratio which is an indicator of stress and the number of granulocytes was quantified since granulocyte counts is an indicator of parasite infestation;
(3) Electrophoresis of the blood proteins; and
(4) Levels of T4 (corticosterone)

The hens that had their blood taken were also sacrificed and an autopsy was performed on each hen. This autopsy also included for the visit 1 hens which were sacrificed, a removal of a trace of the mucosa Caecal from the wall of the Caecal which was taken and placed in 10% formalin and a histopathologic evaluation was performed. For the hens that were sacrificed on visit 2, the wall of the gizzard and a hepatic lobe were removed to clarify the origin of the cahectic state which is indicative of a massive bile reflux in the light of the gizzard, observed in certain hens in row 4. The results of this analysis permitted the evaluation of the impact of parasites for the occurrence of opportunistic ailments and provides some information concerning the physiological state of the hens.

Zootechnoloical Parameters

The zootechnological parameters that were undertaken in this study were the following:

(1) amount of food consumption;
(2) number of eggs that were laid;
(3) weight of the eggs;
(4) number of eggs that were broken; and
(5) consumption of water per hen.

Evaluation of the Results

To calculate the amount of infestation, an estimation of the total linear surface of the hen house was undertaken as well as the material in the hen house. After taking these measurements, a measurement of mean diameter of the colonies observed and the frequency of repetition in similar zones was determined. All of these measurements permitted the calculation of the mean concentration of arachnids per $cm^2$ for each hen house. This value was then compared to a semi-logarithmic scale of 8 units. The grade of infestation was then obtained on a scale of 0 to 8. The grade 8 was assigned when there were more than 400 arachnids per $cm^2$ and is indicative of the maximum amount of infestation of arachnids in a henhouse.

To estimate the evolution of the number of parasites, seven types of different measurements were taken for each row, to have the best estimation possible for the evolution of the parasitic population for the hen house studied. The measurements that were taken were:

(1) the number of colonies per cage;
(2) the diameter of the colonies observed;
(3) the degree of infestation of ground droppings;
(4) the degree of infestation on the eggs which were collected;
(5) the infestations on the structures of the hen house (cages, pipes, etc.);
(6) the number of cages that were infested; and
(7) the degree of mean infestation in each row.

Figure 16:
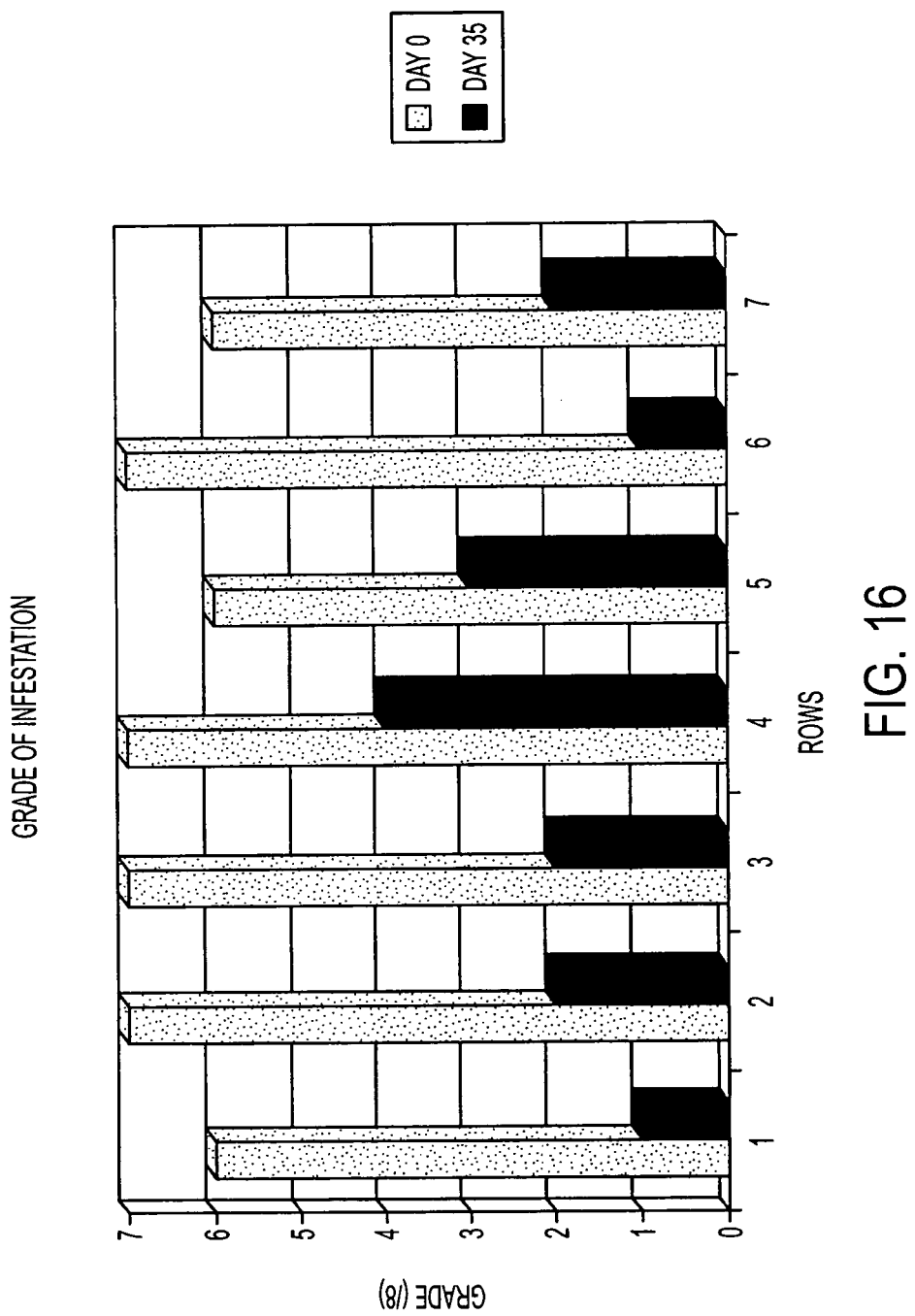
FIG. 16 is a graph showing the grade of infestation on Day 0 prior to treatment and Day 25 after treatment with duck repulsive allomone (DRA) of chicken mites for each of the seven rows of hens treated.

For each row and for each of the values a very clear diminution was observed for each of the parameters of the parasites that were measured. The grade of infestation in the hen house of 6.5 was diminished to 2 (FIG. 16). In 5 weeks a decrease of arachnid infestation to an infestation level of 2 was shown using the DRA product.

The first measurements that were effectuated to directly evaluate the number of cages that were infested with arachnids, the number of colonies of arachnids present and the diameters of the arachnids. These measurements possess a double advantage since they can be easily obtained and also serve as a personal reference for the aviculturist to estimate their amount of infestation in the hen houses. Also reported were measurements based on a strong or weak infestation. This data permits the aviculturist to estimate the infestation in a nonprejudicial manner and to determine whether the infestation level of 2 is surpassed. To the contrary, if the grade of infestation passes 5 or more, the aviculturists estimate is very important and a treatment against the arachnids should be started.

Figure 17:
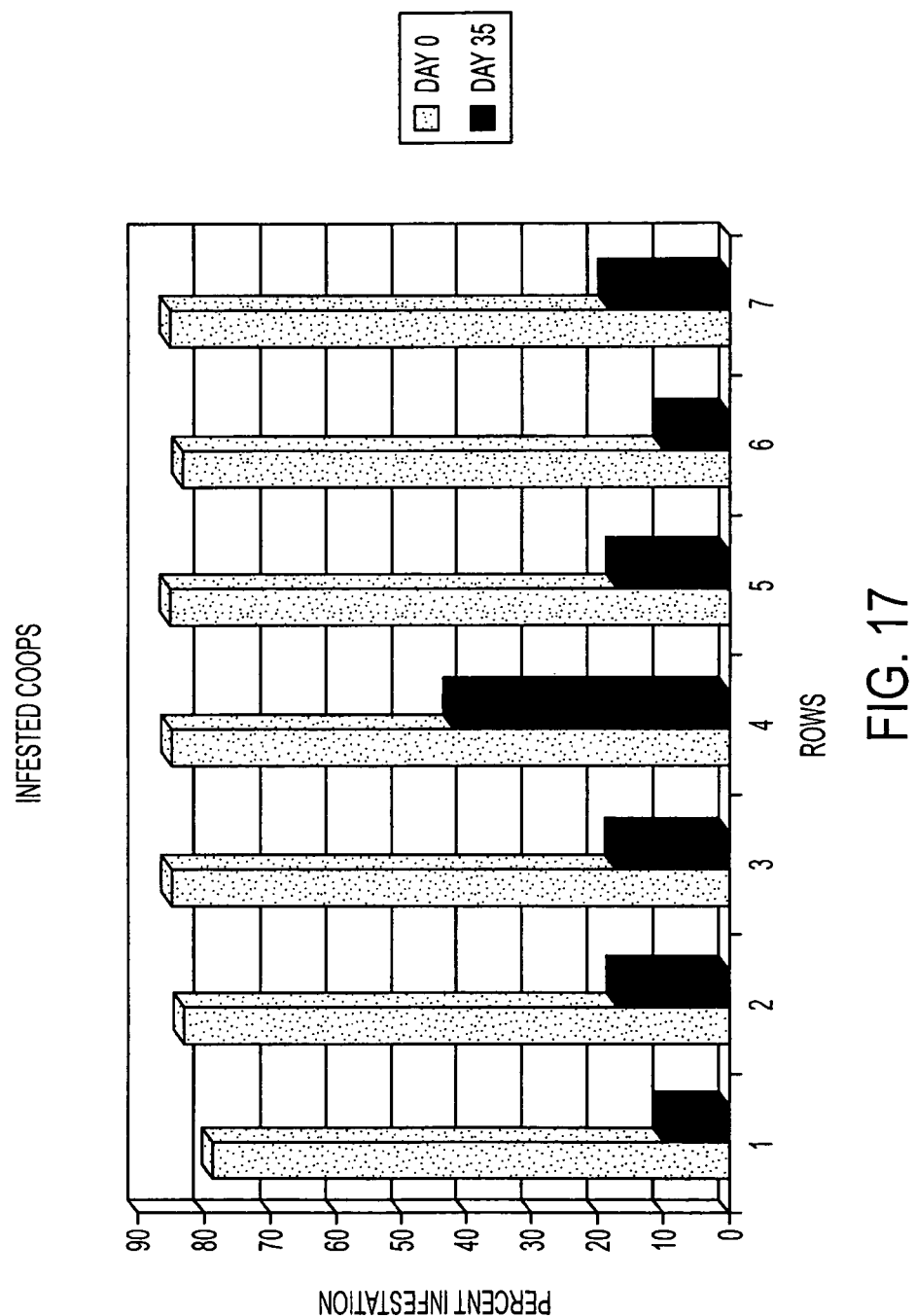
FIG. 17 is a graph showing the percent of infestation of chicken mites in each cage (coop) for each of the seven rows of hens at day 0 (untreated) and at day 35 after treatment with duck repulsive allomone (DRA).
Figure 18:
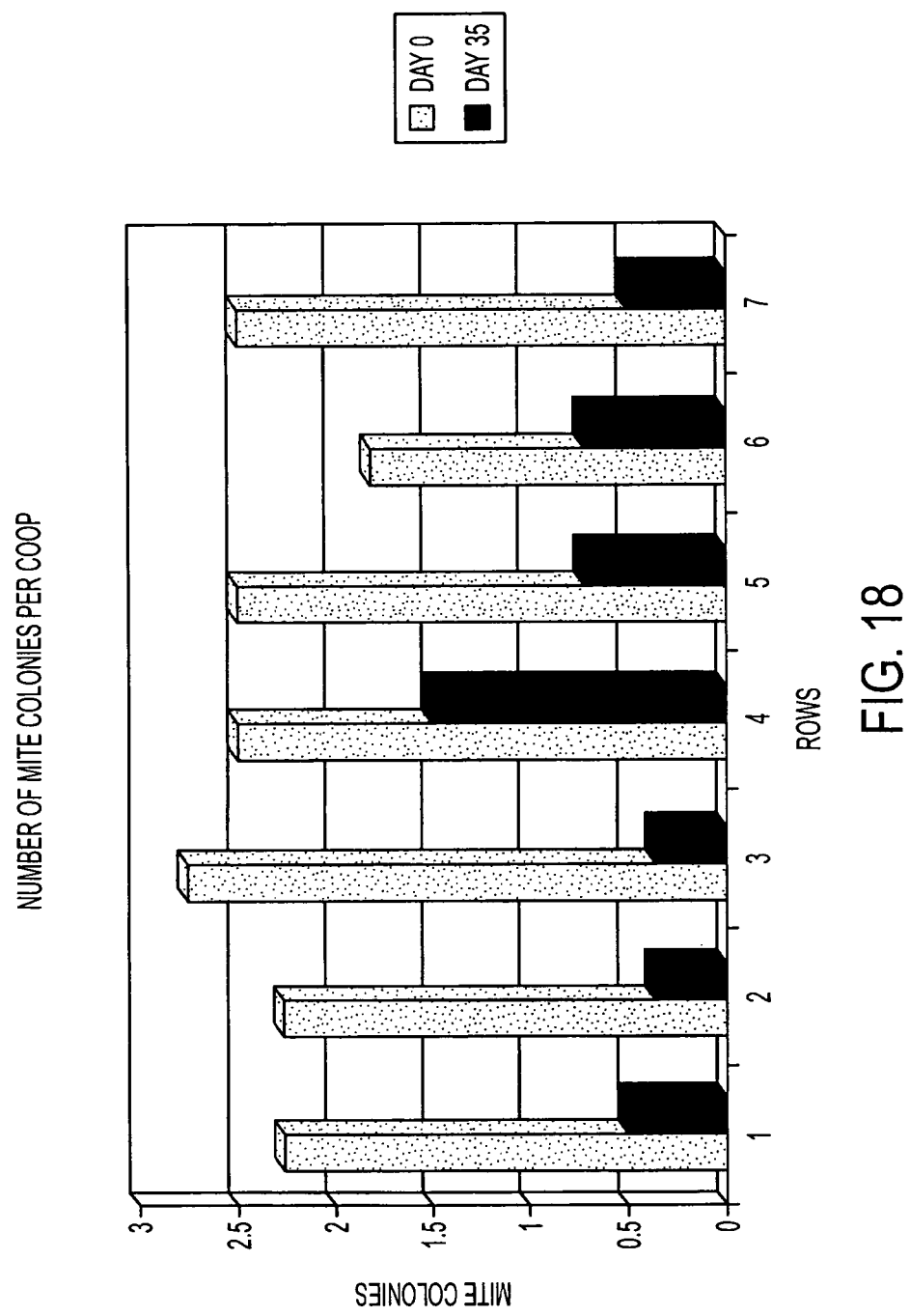
FIG. 18 is a graph showing the number of colonies per cage (coop) of chicken mites on Day 0 prior to treatment and Day 35 after treatment with duck repulsive allomone (DRA) in the seven rows of hens that were tested.
Figure 19:
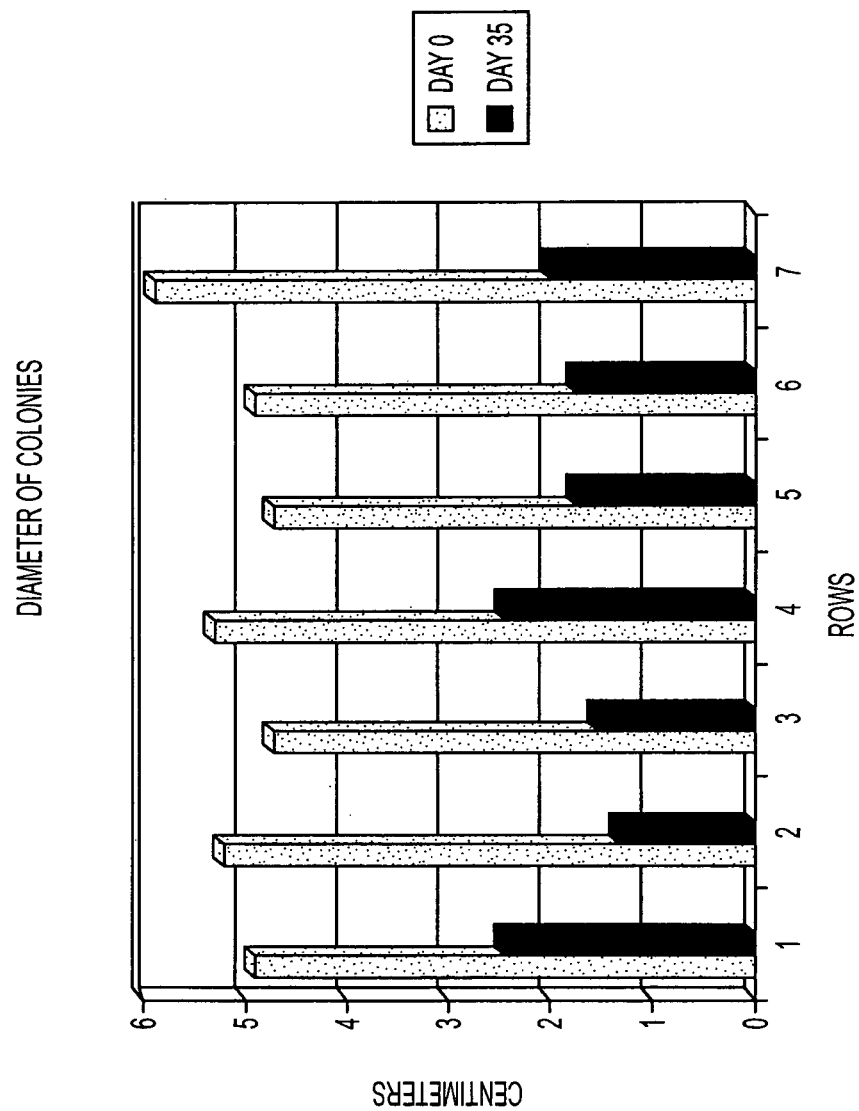
FIG. 19 is a graph showing the diameter of the chicken mites on Day 0 prior to treatment and Day 35 after treatment with duck repulsive allomone (DRA) for the seven rows of hens that were tested.

In the V1 visit it was noted that more than 80% of the cages were infested with a mean of 2.5 colonies per cage and the diameters of the arachnids had an average of 5 cm. After the final visit 2, the percentage of cages which were infested, fell from 80% to 18% with a mean average of 0.5 per cage and colonies having a diameter of 5 fell to 1.5 cm (FIGS. 17, 18 and 19).

There was also an interest in measuring the amount of infestations of arachnids in the structure in the hen house. For this type of measurement, the degree of infestation of the structures was measured by collecting the droppings and evaluating the number of arachnids, collecting the eggs and counting the number of arachnids and counting the arachnids on other structures of the hen house such as the walls, in the animal feed and the like. The measurements were taken to evaluate whether the DRA product solely repels the parasites from the cages, but also whether DRA destroys the chicken mites inhabitant or their feeding environment.

The degree of infestation was evaluated by collecting the droppings from the floor. The dry droppings are privileged hiding place for the parasites and their evacuation from the hen house risks recontamination of the other hen houses with the parasites. The results also showed that the DRA product prevents the *Dermanyssus* to eat. Once an arachnid population is reformed in the middle of the hen house, recontamination is unavoidable.

Figure 20:
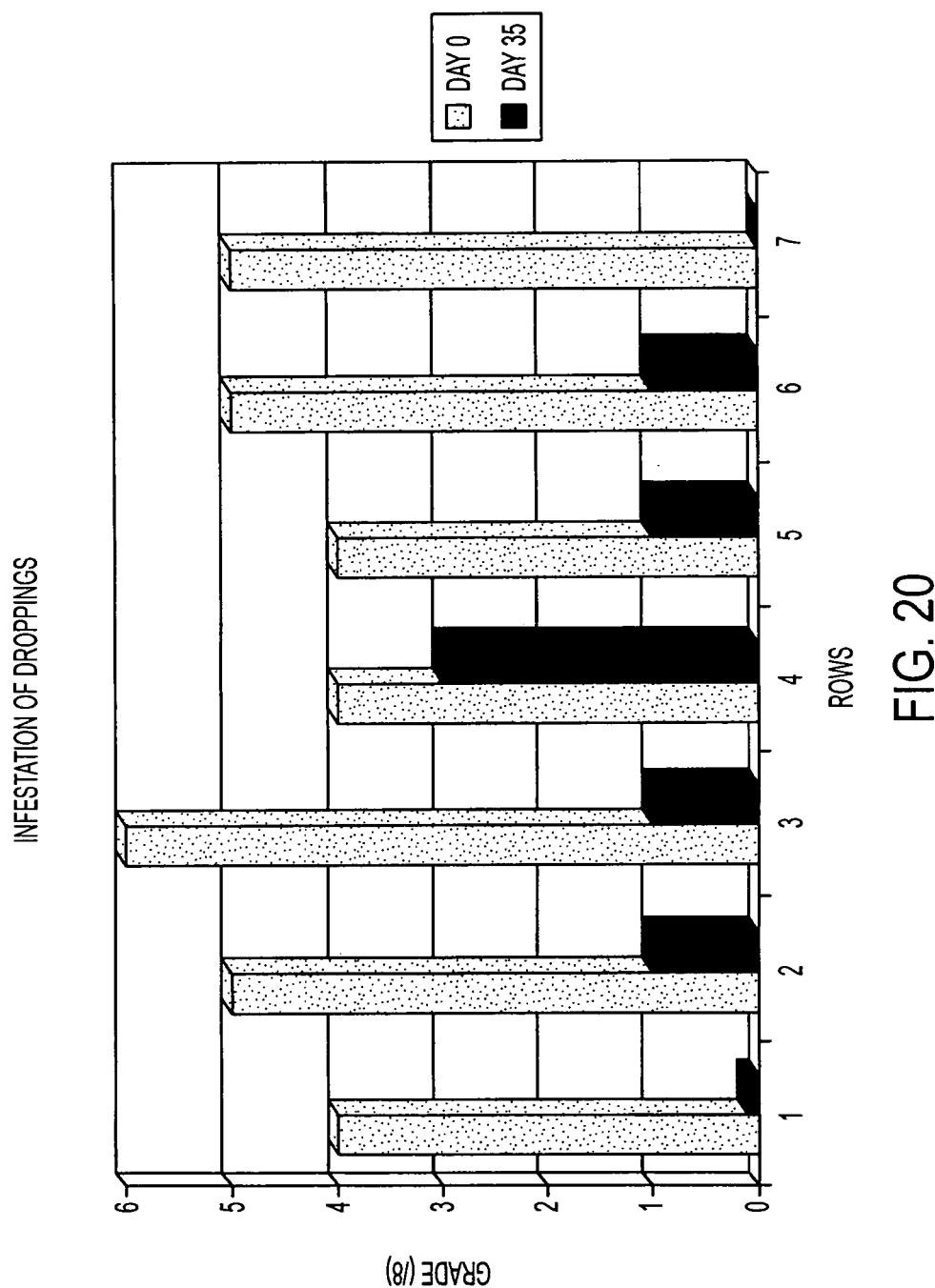
FIG. 20 is a graph showing the infestation of the droppings of the hens on Day 0 prior to treatment and on Day 35, after treatment with duck repulsive allomone (DRA) for the seven rows of hens that were tested.

FIG. 20 shows the data obtained and the efficacy of the DRA product of the present invention on the hen house of the gathered droppings which shows a mean average grade of infestation of 5 prior to the treatment to a grade of infestation inferior to 1 after the treatment.

Figure 21:
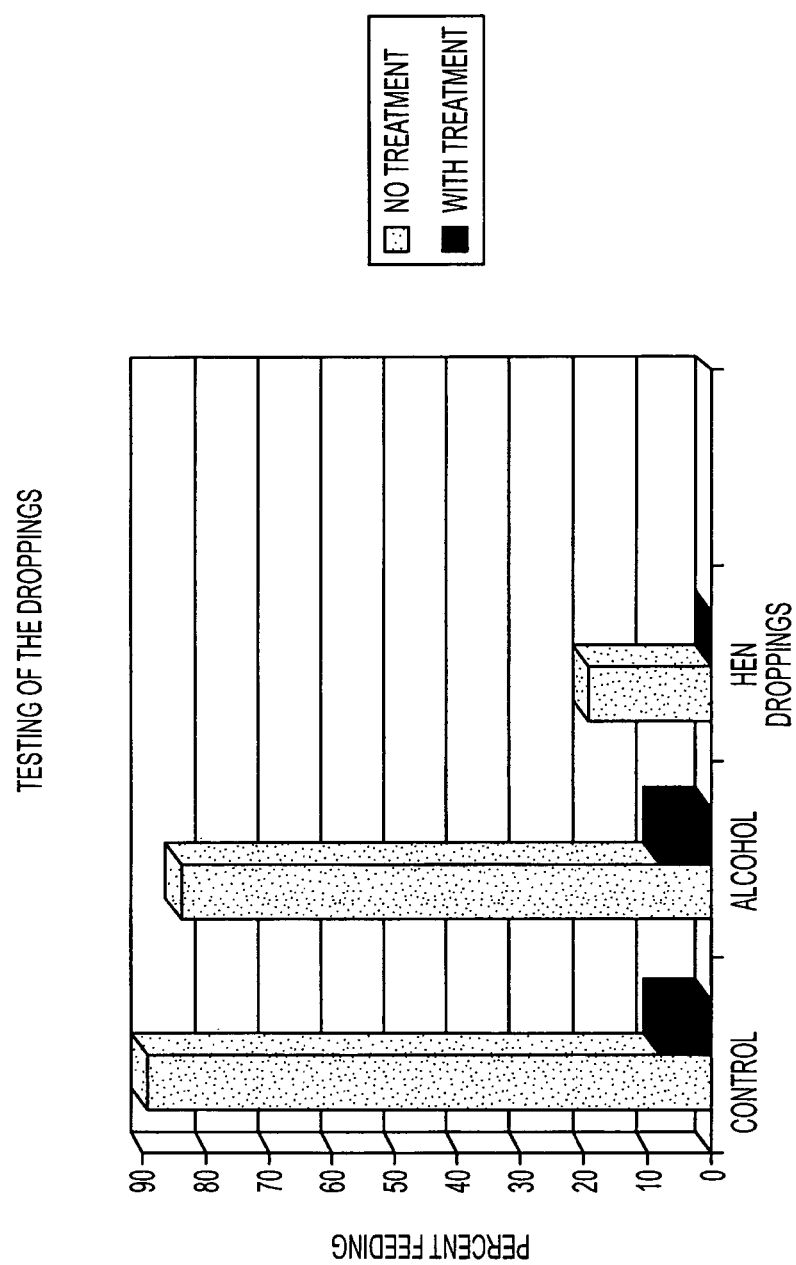
FIG. 21 is a graph showing the percent feeding of chicken mites on chicks with the duck repulsive allomone (DRA) extracted from the hen droppings. The DRA product was extracted with alcohol.

The droppings were tested to see whether they repulsed arachnids in a laboratory. The results are set forth in FIG. 21 in which the data shows that an extract of alcohol from the droppings prevented arachnids from feeding of the skin of a chick utilized for these tests in vitro.

Figure 22:
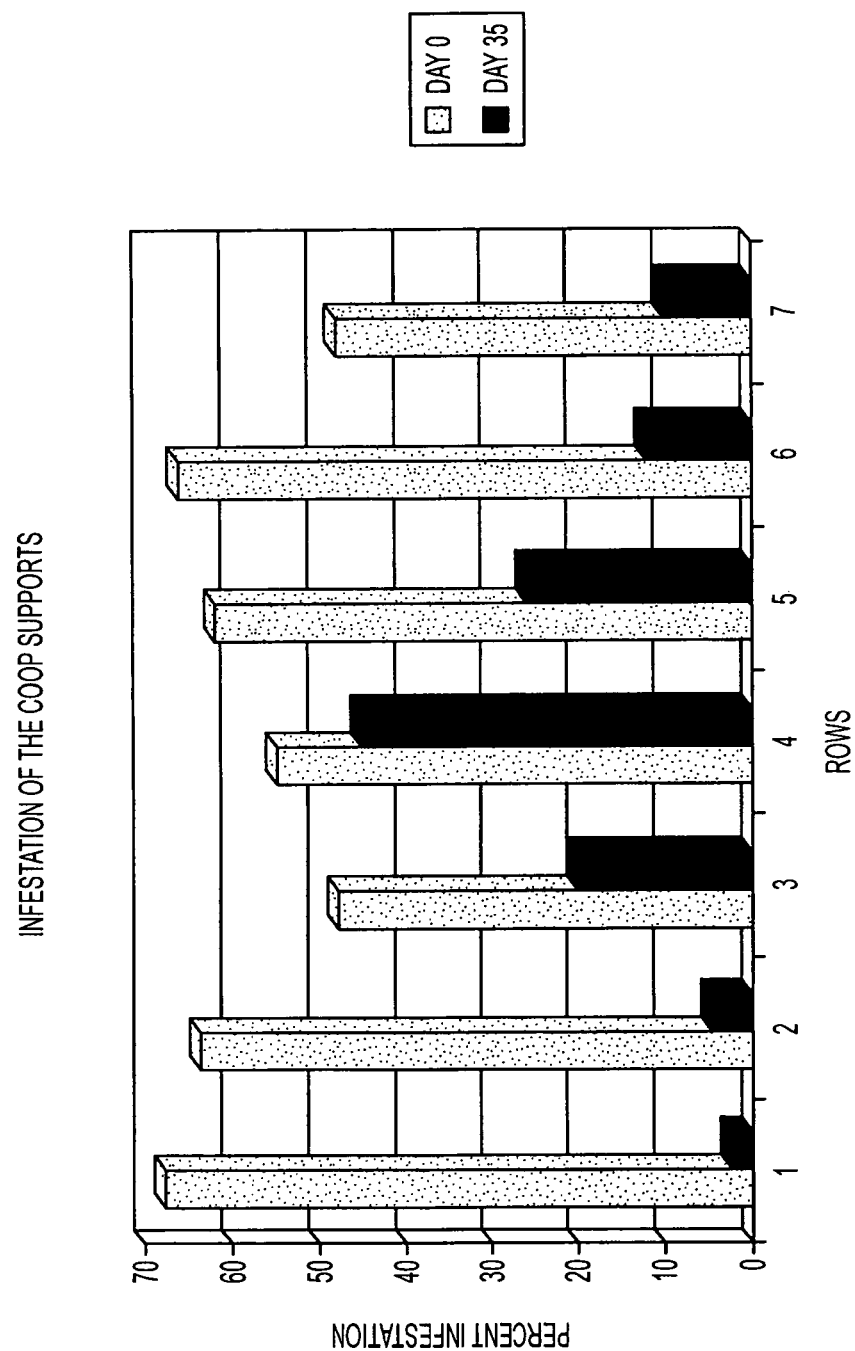
FIG. 22 is a graph showing the percent of infestation of chicken mites in cage (coop) supports for each of the seven rows of hens at day 0 (untreated) and at day 35 after treatment with the duck repulsive allomone (DRA).

As far as the eggs and the other structures in the hen house were concerned a clear diminution of the mean percentage of infestation of arachnids was observed. For the infestation of the eggs, on the first visit a rate of infestation was 64% and dropped to 14% after treatment with the DRA product of the present invention. For infestation of the structures in the hen house an infestation rate of 57% was determined on the first visit and dropped to 12% after treatment (FIG. 22).

In a global manner, a drop in the amount of parasites from 6.5 to 2 in the hen houses was observed.

Evaluation of the Parasitic Population

Number 2 nymphs were evaluated since this is an intermediate stage in development of arachnids in which the number 2 nymphs are very sensitive to fasting, as well as the fact that their presence signals an expansion of the colony. The analysis of the adult population clarifies the evolutionary dynamics of the colonies. In particular, the percentage of type 2 female nymphs is very interesting. These females are larger than the type 1 female and have a brownish red to black coloring. They also possess an egg that is visible to the naked eye. This egg is not laid in the absence of male adults but in the presence of types females and produces a new male for the origin of a new colony. The females die after laying their egg. Their prevalence amongst adults signals a state of degradation of the colonies with the disappearance of the two sexes. This situation is followed by a dispersion of the colonies.

In visit 1, the demography of the parasites in the hen house corresponded effectively to a demography that was expanding with the majority of deutonymphs at the deutonymphal stage. On the second visit, the parasitic population was in a demography of regression. Notably more than 87% of the arachnids present in the colony after the second visit were dead in comparison with less than 7% after the first visit. Also the nymphs at stage N2 were absent from the sampling in visit 2. This indicated that the mite population was stopped and in regression. It was also observed during visit 2 that there were numerous type 2 females. None of the type 2 females were found in the center of the colonies, which is their usual habit. The females of type 2 were erratically found in a pile around the type 1 nymphs.

Another parameter was to measure the number of mites that were feeding and therefore had a red color. On visit 1, 80% of the population had a red color. On visit 2, only row 4 had several mites with a red color.

Tests Parasitic In Vitro

Three parameters were tested: the presence of DRA in the droppings, the present of DRA in the uropygial gland secretions of the hens that were sacrificed at visit 2 and the sensitivity of the mites present in the hen house.

Presence of DRA in the Droppings

Hen droppings taken from the hen house were extracted using alcohol. The extracts of the hen droppings that were treated with DRA were applied to the skin of the chicks and protected the chicks against *Dermanyssus gallinae*. The skin of the control chicks were bitten by 90% of the mites, while the skin of the chicks treated with the alcoholic extract of hen droppings were bitten in 20% of the cases.

Presence of DRA in Uropygial Secretions of Hens on the Second Visit

The uropygial glands of the hens that were sacrificed after visit two were removed and tested for the presence of DRA.

Figure 23:
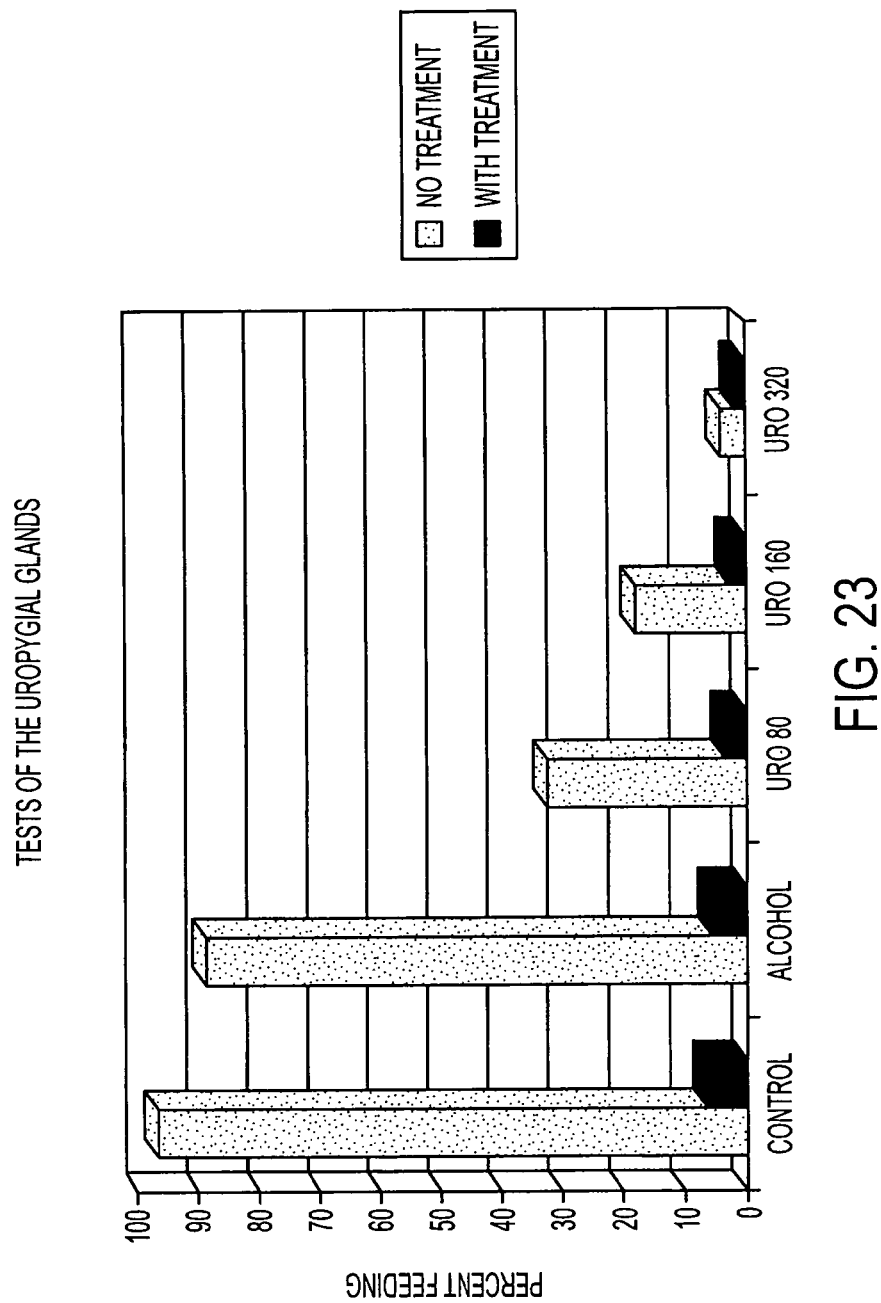
FIG. 23 is a graph showing the percent feeding of chicken mites on chicks which were treated with the duck repulsive allomone (DRA) at different dilutions extracted from the uropygial glands of autopsied hens after treatment on day 35.

FIG. 23 shows the results when the DRA was tested at different concentrations. A dilution of 160 was very repulsive. A dilution of 320 was also efficient and it can be concluded that the DRA product was not only present in the uropygial gland of the hen, but also at a concentration that it is normally found in the gland of ducks.

Other Tests

Tests for Resistance to Other Miticides

Other miticides were tested for their efficiency and the results are shown in the following Table 8:

TABLE 8

| Active Material | % deaths 1× dose | % deaths 4× dose | % deaths 8× dose | % deaths 16× dose | % deaths 32× Dose |
|---|---|---|---|---|---|
| Trichlorfon | 20.4 | 39.7 | 34.4 | 80.8 | 94.4 |
| Amitraz | 97.4 | 98.5 | 100.00 | 100.00 | 100.0 |
| Azamethiphos | 30.0 | 43.3 | 54.8 | 100.00 | 97.8 |
| Aplhamethrine | 48.1 | 85.2 | 97.0 | 98.9 | 99.6 |
| Carbaryl | 19.3 | 37.8 | 64.4 | 91.1 | 97.8 |
| Control | 0.4 | 0.7 | 0.0 | 0 | 1.1 |

The doses were chosen at 1 to 32 times the dose commercially given on the products' instructions. Amitraze was the most efficient miticide at the prescribed dose. All of the other miticides tested had a performance of less than 50% mortality rate. At four times the dose, Aphamethrine had an 85% efficacy rate. However, in these commercial products only 16 times the recommended dosage was effective to kill the chicken mites. Even if the products were effective it was noted that the colonies had a tendency to reform after the treatment.

Feeding of the Mites Harvested on Visit 2 and Demographic Growth in the Laboratory The results mentioned in this section are only qualitative and are only a comparison of the evolution of the grade of infestation of a hen cage using a living host. Two populations of mites having a similar size (grade 4) were placed in two distinct chicken cages with a live chick. The first population was the control in which no treatment with DRA was administered and the *Dermanyssus* that were used in this example were obtained from a different source. The second chicken cage contained *Dermanyssus* that were collected from the hen house that was treated after visit 2.

In two weeks, the control population had an increase of two points on the graduation scale than the visit 2 population. The virulence of the chicken mites in the control group at a grade 4 resulted in the chicks dying, while with the visit 2 population of mites, the chicks survived.

Social Behavior

After the 5$^{th}$ day of treatment, it was observed that the migration of the colonies of mites was constant. These observations were confirmed in a laboratory with the chicken mites from visit 2. It was not possible to find stable colonies in the test tube experiments that were performed. Only continual migration was observed.

The visit 2 chicken mites were introduced into the control colonies of mites and it was observed that there was disorganization of the colonies that could not reach reconstruction.

Study of the Chromatographic Profiles of the Cuticle of the Visit 2 Mites

Figure 24:
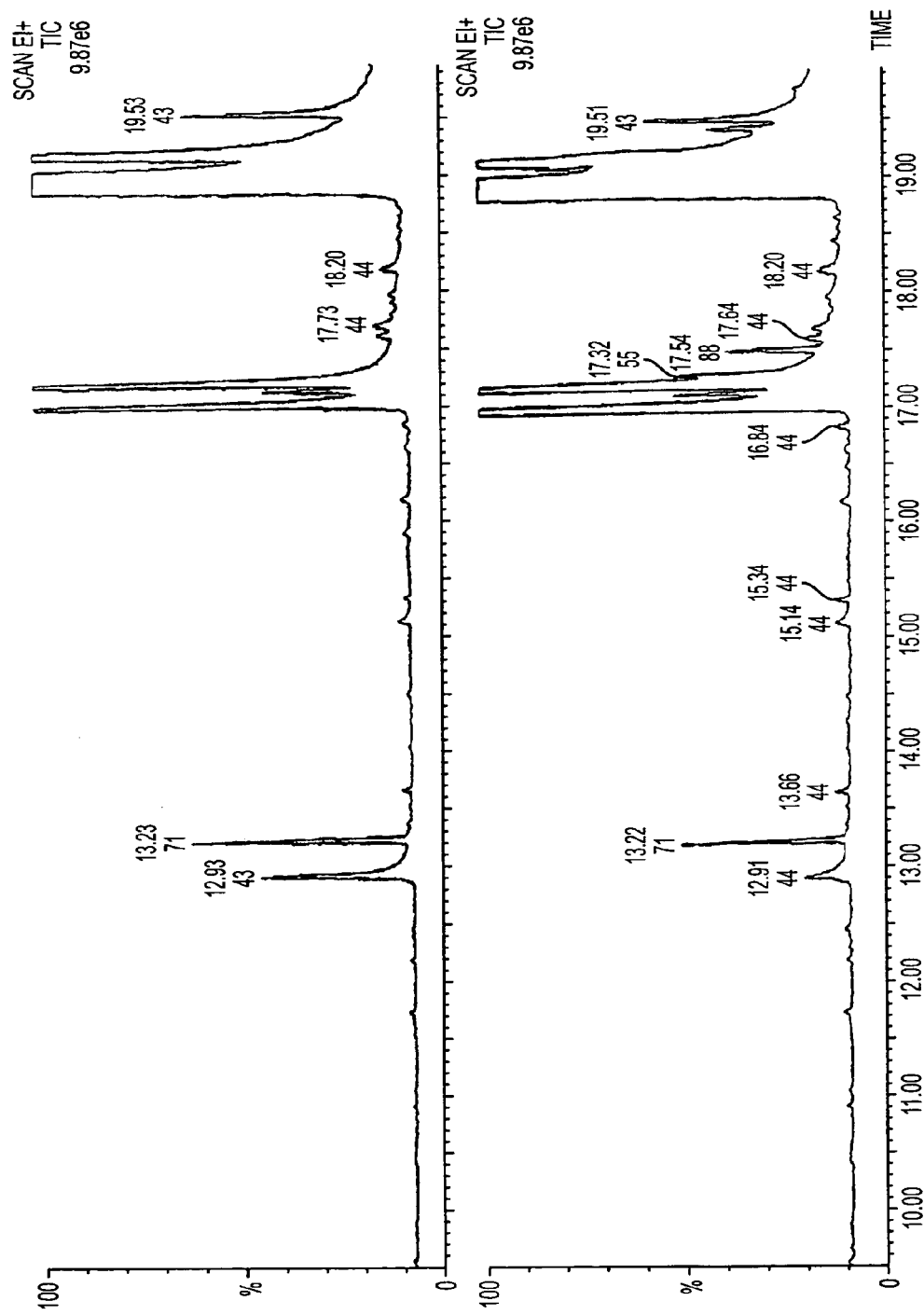
FIG. 24 is a GC/MS spectrograph of the duck repulsive allomone (DRA) extracted from hens that were autopsied at 35 days after treatment. The peak for DRA can be seen around 13.23 on this spectrograph.

The *Dermanyssus* from visit 2 were killed by immersion in $CO_2$ at −78° C. to provoke a brutal death without draining their digestive tubes. The chicken mites were then placed in dichloromethane and the analysis of the solvent was performed using GC/MS. The chromatographs are illustrated in FIG. 24 and show the two peaks characteristic of DRA. (at 13.23) The adsorption of the two molecules which are strongly hydrophobic by the cuticle of the mites was not surprising since the cuticles of mites have a structure that has a high affinity for hydrophobic compositions.

Medical Parameters of the Hens Blood

The analysis of blood taken from the hens at visit 1 and visit 2 had notable differences with respect to the 35 days of treatment. Table 9 below illustrates the results of the blood tests at visit 1 and visit 2 and the average and variations (a) were calculated.

As can be seen in this Table a significant augmentation in the hematocrit was observed for this physiologic value. The value observed at visit 1 was extremely low and comprised values ranging from 19.73% to 27.77%, which values are inferior to the physiologic normal value of 30%. The hematocrit value reflects the loss of blood which is important and not compatible with the production of correct eggs. In contrast the hematocrit from the treated hens from visit 2 had values between 31.42% to 39.78%, which are normal values and thus reflect that the treatment with DRA resulted in the inhibition of feeding of the *Dermanyssus* and thus the loss of blood does not occur in the treated hens.

The lower levels of the granulocytes from the blood of the DRA treated hens in visit 2 as compared with visit 1 confirm the regression of chicken mite infestation. A drastic diminution of granulocytes and eosiniphils is indicative of the lowering of the disturbance of the hens introduced by the biting of the chicken mites, which results in an inflammatory response or a state of stress introduced by repeated irritation.

The results of the leucocytes/lymphocytes is considered as a reliable medical indication of stress and this value was significantly lower in the blood taken from the hens at visit 2 as compared to the blood taken from the hens at visit 1 which were not treated with DRA.

TABLE 9

| | Normal Biological Values (%) | Values at Visit 1 (%) | Values at Visit 2 (%) |
|---|---|---|---|
| Granulocytes neutrophils Non-segmented nucleus | 0-6 | 5.53 (σ = 1.125) | 1.2 (σ = 1.320)* |
| Granulocytes neutrophils segmented nucleus | 60-75 | 71.13 (σ = 18.71) | 57.4 (σ = 15.76)* |
| Eosinophils | 0-4 | 1.20 (σ = 0.55) | 0.32 (σ = 0.23)* |
| Basophils | 0-1 | 0.08 (σ = 0.12) | 0.22 (σ = 0.12) |
| Macrophages | 0-5 | 1.69 (σ = 0.10) | 2.11 (σ = 0.57) |
| Lymphocytes | 15-30 | 21.36 σ = 1.91 | 16.87 (σ = 1.65 |
| Ratio Leucocytes/lymphocytes | <0.55 (±0.27) | 0.32 (σ = 0.06) | 0.10 (σ = 0.07)* |
| hematocrit | 30-40 | 22.8 (σ = 3.00) | 35.2 (σ = 4.61)* | where * means that the differences between the means are statistically significant (student t-test (n = 28) (p < 0.01).

Electrophoresis of the Blood Proteins of Hens

Electrophoresis was performed on the blood taken from the hens at visit 1 and visit 2 to determine the blood protein content of the samples.

Table 10 below shows the ratio between albumin/globulins (A/G) that evaluates the inflammation in the animals. This Table reflects the values obtained from visit 1 (V1) and visit 2 (V2).

TABLE 10

| Visit 1 (V1) | Visit 2 (V2) |
|---|---|
| 0.15 | 0.99 |
| 0.53 | 0.98 |
| 0.34 | 0.76 |
| 0.53 | 0.78 |
| 0.41 | 1.05 |
| 0.58 | 0.97 |
| 0.39 | 1.02 |
| 0.73 | 0.93 |
| 0.28 | 1.05 |
| 0.66 | 0.93 |
| 0.50 | 0.90 |
| 0.46 | 0.79 |
| 0.38 | 0.80 |
| 0.61 | |

The mean value for the A/G ration is 0.46 for V1 and 0.92 for V2. The normal value which is published is 0.71 (Sturkie and Newman 1951). Thus, these results illustrate that there was more inflammation in the hens that were not treated with DRA than the hens that were treated with DRA.

Autopsy Results

The visit 1 hens that were sacrificed and subjected to an autopsy revealed that there were no anomalies of the 14 autopsies performed outside of scratching lesions presented in the auxiliary region and which appeared on the rump of many hens. The histopathic examinations of the caecum were normal. The uropygial glands of the birds were examined and appeared normal in size and the content conformed to that which was habitually observed in this species; i.e., they contained yellow oil and had translucent little globules of wax.

The visit 2 hens that were autopsied did not have any macroscopic anomaly. The uropygial glands were very voluminous. Their content was very different from that described above for the visit 1 hens; it was very oleaginous and had an amber to orange opaque color. The appearance of the uropygial gland of the visit 2 hens is the same that was observed in the duck. The secretions were taken and used in the in vitro feeding tests described above.

During the trial the investigators noticed a high mortality rate for those hens in row 4. The hens in row 4 had a phase of anorexia accompanied by sleeplessness before dying. Three additional autopsies were performed on the dead hens from row 4. These hens were cachectic and had a muscular atrophy particularly noticeable on their sternum muscles. Also noted was uterine regression and the mature follicles were blocked.

The gizzard was examined in the sacrificed hens from row 4. The cavity of the gizzards contained the exterior of cereal and several fragments of food which were difficult to identify. The content of the gizzards was saturated with bile and contained a green content, which was the same for the mucous membrane. This indicated that the hens fasted from food. The hepatic parenchymal of two of the hens had a tanned aspect which is however not the tanned aspect which is typical of hens infected by *Salmonella*.

Zootechnical Parameters

The Production of Eggs

Figure 25:
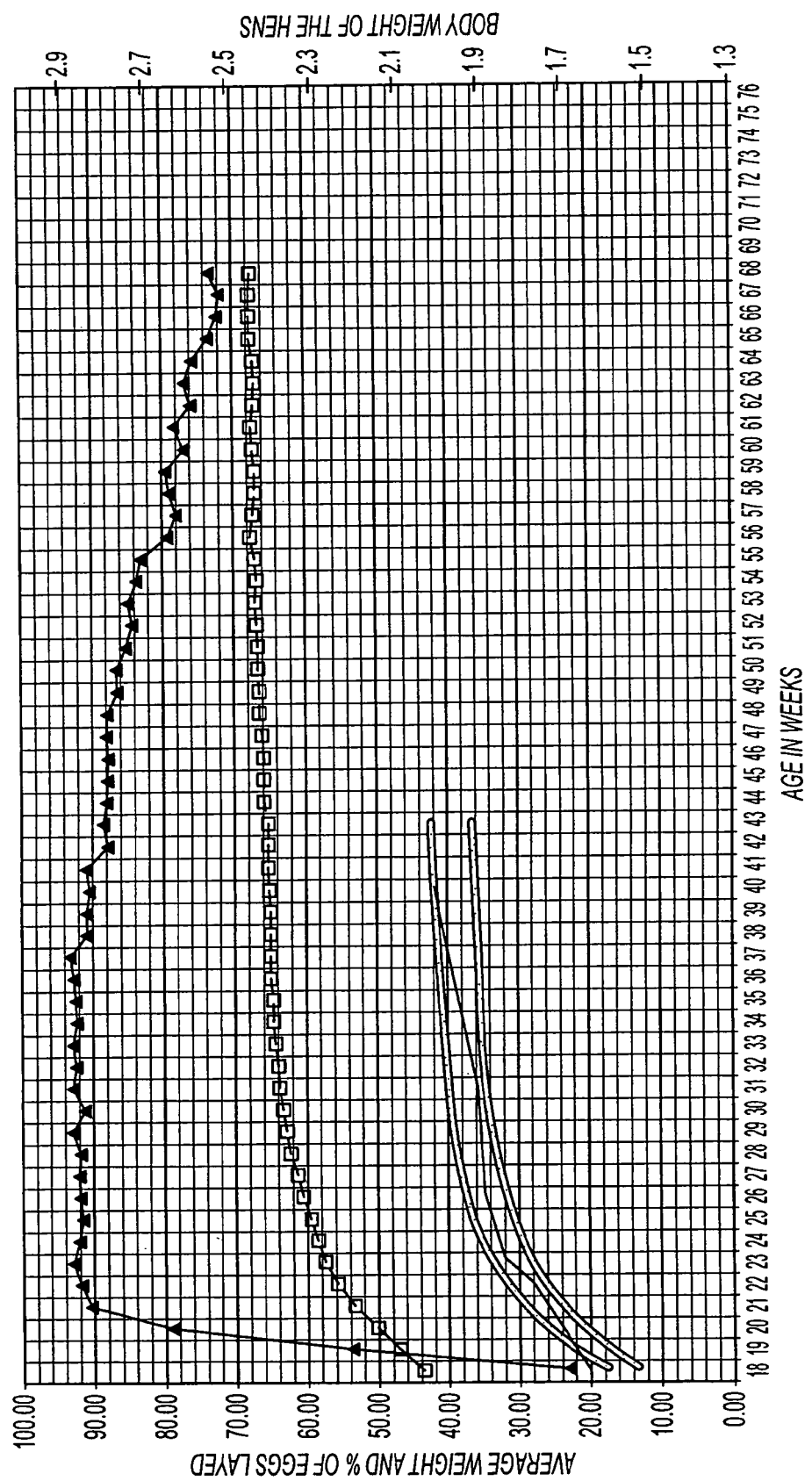
FIG. 25 is a curve showing the amount of egg production of the hens treated with duck repulsive allomone (DRA). Δ represents the percent age of eggs that were laid; ☐ represent the average egg weight; - - - represents the hen live weight (LW); and, represents the theoretical hen live weight (LW).
Figure 26:
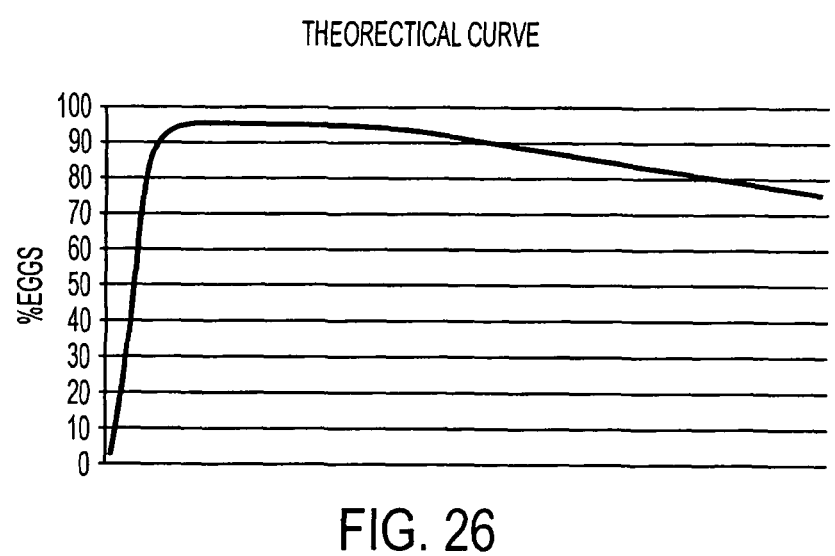
FIG. 26 is a theoretical curve of the egg production of normal hens that were not treated with duck repulsive allomone (DRA).

The production of eggs was also analyzed and the results are presented in FIG. 25.

As can be indicted from this figure, the curve of egg production from the hens in this trial had a tendency to follow a theoretical curve as set forth in FIG. 24. As can be seen from this figure, after a strong start and an early peak of egg production, the production of eggs was diminished rapidly and rested constant underneath the theoretical curve with a important fall around 55 weeks of the hens age. Another global observation that was effectuated was the weight of the collected eggs with respect to the theoretical weight. This curve overtakes the first curve. In affect, the weight of the eggs is under the theoretical normal, but the weight of the eggs for each hen is normal.

The rate of the collected down-classed eggs is a variable that is interesting to observe because it is a principal component of the profitability of the group of hens. The mean results before and after treatment permits one to observe an augmentation in the ratio of eggs which were down-classed.

The five last weeks during the duration of the treatment, one observes an augmentation in egg production compared to the normal egg production. The ratio of the eggs that were down-classed rises slightly in the two first weeks of the treatment with DRA then reaches a plateau and the size then rises at the end to generally pass 15%.

The mean weight of the eggs decreases after 4 weeks with the start of the treatment of DRA. This margin is not significant, but is interesting since the FIG. 25 permits a comparison of the weight of the produced eggs before and after the treatment which shows the augmentation of the mean weight of the eggs.

The quantity of food eaten by the hens by day also recedes for the hens in the course of the treatment with DRA. One can make the following two hypotheses concerning this situation:

DRA in the water of the hens perturbs the hens due to the different taste of the water or digestive problems associated with taking the treatment. However, the quantity of water which was consumed per day was constant. One could think that DRA has a craving influence on the hens, which is not the case. The production of eggs (weight/down classed/size of the egg) was very favorable using the DRA treatment. DRA permits the diminution of food consumption by the hens and maintains the production classic where the lowering of the Food Consumption Index augments the raw margin of the hen breeder.

The amount of mortality of the hens conforms to the normal range of a hen laying farm.

Discussion of Results

Parasitological Results

The entire parasitological results show an important regression of the population of *Dermanyssus* in the course of the testing with DRA. This regression, following the kinetics which was observed during the assays in vitro, started on the fifth day of the treatment. The invasion of the parasitic population starts by the vulnerable stages that are the nymphs N2 stage then the females of type 1 and then the males. The forms of resistance in the nymphs N1 type and females of type 2 show a significant survivorship that diminished and associated with major modifications in the social behavior. The apparent incapacity of these chicken mites to regroup in structural colonies around the females of type 2 that is habitually observed, resembles a diminution of their hope of life.

The tests concerning the feeding of the mites in vitro with the uropygial secretions taken from visit 2 (V2) confirm the presence of DRA in the secretions and confirm the choice of administration. The components of DRA after reabsorption by the digestive tract are excreted by the uropygial gland.

The results obtained for row 4 did not correlate with the results obtained for the other rows. It appears that the treatment in row 4 commenced about 2 weeks after the others rows, since the presence of two liquid phases in the water recipient was in fact observed. The supernatant observed in the water reservoirs was rainbow colored, covered the total surface and neatly adhered to the inner wall of the water reservoir. An analysis of a sample taken from the reservoir in row 4 by chromatography confirmed that it was DRA.

Furthermore, the water reservoir in row 4 had more calcium deposits than in the other 6 reservoirs. Also green algae were colonizing in this reservoir in certain calcium deposits. This water reservoir was also placed just next to the ventilation system of the air conditioning and temperature of the water was elevated. Thus, the difference in the water reservoir in row 4 accounts for the differences obtained in the results as compared to the other DRA treated rows.

Medical Parameters

These results were consistent with the parasitological results. The inhibition of the behavior of feeding of the chicken mites showed a term of lack of blood and the immune process was provoked by the repetitive bites which regressed with the DRA treatment. The study of these parameters also permits to underline the amelioration of the well being of the hen as indicated in the leucocyteflymphocyte and hematocrit results. This amelioration of the physiological parameters favorized better egg production and less morbidity.

The Parameters Zootechnical

The age of the hens treated and also the duration of the assay (limited by the culling of the livestock) did not permit any statistically significant analysis of the results. However, the trend which was observed in those parameters that were measured in the livestock highly parasitic in *Dermanyssus* was encouraging.

The therapeutic implications of DRA are limited to the parasitological domain. The zootechnical results are in fact indicative of the suppression of the chicken mites when DRA is administered.

In the USA the means of production are calculated with a base of the amount of production per year recently furnished in the "Grand Consortiums of the Laying Hen." Thus, in 1987, already 92% of the American farms could be considered infested by *Ornithonyssus sylviarum*. Hinkle had deduced that 92% of the amount of production that were furnished is the amounts corresponding to the animals that were parasitic. For this author, it is not that normal a situation.

Example 18

The objective of this example was to test the efficacy of DRA in hen houses with egg laying hens. This trial lasted for a duration of 4 weeks. In this example, 6 buildings, B1 to B6 housing 31,000 hens per building were used. The hens utilized in this example were Isabrown (brown egg laying) hens. The age of the hens differed in the buildings. In buildings 1, 2 and 3 (referred to hereafter as 131, B2 and 133) the hens had an age of 29 weeks, while in building 4, 5 and 6 (referred to hereafter as B4, B5 and 136) the hens had an age of 57 weeks.

Treatment

Each building was treated independent of the other 5 buildings. For the building B1 an assay was effectuated with a pulverization of the DRA using a thermonebulizer of 12 ml of DRA (50% (w %/w %) of bis(2-ethylhexyl) adipate and 50% (w %/w %) 2,2,4 trimethyl 1,3, pentandiol diisobutyrate) at a 4% (w %/w %) concentration diluted in 12 liters of product into the thermonebulizer and 3 reservoirs were maintained in this building.

For buildings 2 to 6, the DRA (50% (w %/w %) of bis(2-ethylhexyl) adipate and 50% (w %/w %) 2,2,4 trimethyl 1,3, pentandiol diisobutyrate) at a 4% (w %/w %) concentration was administered in the drinking water. This provides the treatment nonstop to the hens and the duration of treatment varied as indicated in the following Table 11. For the buildings B2 and B6, a second treatment was undertaken after a control visit at day 15 (15 days after the start of the treatment). The quantities which were distributed for the building B2 to B6 were 50 ml of the DRA in a reservoir of 500 liters. No control was run this example.

TABLE 11

| Building | Treatment | Duration | Quantity |
|---|---|---|---|
| B1 | Pulverization |  | 3 reservoirs |
| B2 | Drinking water | 5 days (+5 days after day 15) | Voluntary |
| B3 | Drinking water | 10 days | Voluntary |
| B4 | Drinking water | 3 days | Voluntary |
| B5 | Drinking water | 5 days | Voluntary |
| B6 | Drinking water | 3 days (+3 days after day 15) | Voluntary |

Food and water was administered to the hens as known in the trade. A visit of control occurred on day 2 and day 15.

The state of infestation of the red chicken mites was determined according to the method of Bruneau at al., *Parasitology*, 123, 583-589 (December 2001). The measure of the state of infestation provided a log scale. The new infestation of 6/8 cannot be measured except in a laboratory. The scale considered as a new infestation of 4/8 is a critical stage for treating the buildings or hen houses.

Blood was drawn from the hens and protein electrophoresis was undertaken. The state of the hens was also evaluated.

Characteristic of the Hen House Buildings

The hen house buildings were infected by red chicken mites for a duration of 7 years prior to this trial. The different solutions to minimize the red chicken mites that were previously utilized were different light cycles of 4 hours on/2 hours off during day and night, treatments (just for 5 flocks) with Sevin, Cepoux and Actograde, which are commercially available products used to treat red chicken mites. The treatments were not successful which has no influence on the hens in this trial.

The buildings were situated as follows:

|  | Corridor | | | | | |
|---|---|---|---|---|---|---|
| egg gathering place | 1 | 2 | 3 | 4 | 5 | 6 |

The evaluation of the grade of infestation of red chicken mites was according to the method of Bruneau, supra. A first evaluation was effectuated in the buildings to verify the state of the infestation of the buildings and the different red chicken mites that were present. After, a diagnostic study of the state of the population of the red chicken mites after their removal from the buildings was effectuated on Day 1 in a laboratory. Two species of chicken mites were present in the hen house buildings *Dermanyssus gallinae* (DG) and *Dermanyssus hirundinis* (DH).

The results of the evaluation are set forth in the following Table 12:

TABLE 12

| Building | % *Dermanyssus gallinae* | Scale of Infestation (#/8) |
|---|---|---|
| B1 | 86 | 3.9 |
| B2 | 97 | 3.4 |
| B3 | 93 | 3.7 |
| B4 | 84 | 5.4 |
| B5 | 89 | 4.2 |
| B6 | 87 | 4.6 |

After about nine weeks, the following observations were made.

Observations and Results

The population of the infestation of the chicken mites did not change during this trial. 85% of the chicken mites present were *Dermanyssus gallinae* and the rest were *Dermanyssus hirundinis*.

Each of the buildings was evaluated and the following results were obtained:

Building 1=The colonies of mites were still there. One noted the amelioration of the situation of the parasites in this building. There were no mites on the collected eggs. Less than 1% of the eggs had spots that were ruined by the mites feeding thereon. In the laboratory the mites appeared perfectly functional; i.e., they flee from light, reform their colonies even though dispersed and eat normally. The treatment is being further checked in this building.

Building 2—One found piles of the red chicken mites, but no colonies. Their presence in marked zones on the first visit of colonies was not present after treatment with DRA. There was no observation of spotted eggs by mites feeding thereon.

The mites did not flee from the light or mechanical stimulation. The mites were also unable to feed.

Building 3—the same observations as in building 2 were noted.

Building 4—the presence of a number of red chicken mites in movement were noted over all the structures of this building. The colonies were in disorganization and were annoyed. A drop in the number of chicken mites in the egg collection building was observed. Many of the eggs were down-classed, on the average 35%. The chicken mites had a tendency to hide out on the ground, which caused multiple risks in that they were crushed in the egg collecting building.

Building 5—same observations as building 4

Building 6—same observations as building 4

The following Table 13 shows the results of the infestation on Day 15:

TABLE 13

| Building | Day 0 (#/8) | Day 15 (#/8) |
|---|---|---|
| B1 | 3.9 | 4.1 |
| B2 | 3.4 | 2.2 |
| B3 | 3.7 | 1.6 |
| B4 | 5.4 | 4.8 |
| B5 | 4.2 | 3.7 |
| B6 | 4.6 | 3.1 |

Only building 1 had a grade of infestation of chicken mites which increased. All of the other buildings treated with the DRA in water reacted in a positive manner to the treatment; i.e., the infestation of the chicken mites decreased.

Evaluation at Day 35

The buildings were also evaluated at Day 35, in a similar manner as described above for Day 15. The following observations were noted:

Buildings B1, B2 and B3: the chicken mites did not react to light or other mechanical stimulation. The mites were incapable of feeding. In Building 1, the colonies reformed at greater than 60% after their desegregation. The reformation of the colonies in building 2 and building 3 did not exceed 60%.

Buildings B4, B5 and B6—The chicken mites did not react to light. The reaction to mechanical stimulus was very little. The threshold of 60% for reformed colonies was exceeded for building 4 and building 6. The infestations were practically identical for B4 and B6 as the 61 building.

The following Table 14 show the results obtained relative to infestation comparing Day 0, Day 15 and Day 35:

TABLE 14

| Building | Day 0 (#/8) | Day 15 (#/8) | Day 35 (#/8) |
|---|---|---|---|
| B1 | 3.9 | 4.1 | 2.4 |
| B2 | 3.4 | 2.2 | 2.3 |
| B3 | 3.7 | 1.6 | 1.9 |
| B4 | 5.4 | 4.8 | 4.5 |
| B5 | 4.2 | 3.7 | 4.1 |
| B6 | 4.6 | 3.1 | 4.1 |

These results indicate that there is a decrease in the amount of red chicken mites with the DRA treatment.

While the invention has been described in terms of various preferred embodiments, the skilled artisan will appreciate that various modifications, substitutions, omissions and changes may be made without departing from the scope thereof. Accordingly, it is intended that the scope of the present invention be limited by the scope of the following claims, including equivalents thereof.

What is claimed is:

1. An arachnids repulsive composition comprising about 45.0% to 55.0% (w %/w %) bis(2-ethylhexyl) adipate and/or derivatives thereof and/or spatial isomers thereof, and about 45.0% to 55.0% (w %/w %) 2,2,4-trimethyl 1,3 pentanediol diisobutyrate and/or derivatives thereof and/or spatial isomers thereof.

2. An arachnids repulsive composition consisting of bis(2-ethylhexyl) adipate and/or derivatives thereof and/or spatial isomers thereof, and 2,2,4-trimethyl 1,3 pentanediol diisobutyrate and/or derivatives thereof and/or spatial isomers thereof.

3. The arachnids repulsive composition according to claim 2, which consists of about 45.0% to 55.0% (w %/w %) bis(2-ethylhexyl) adipate and/or derivatives thereof and/or spatial isomers thereof, and about 45.0% to 55.0% (w %/w %) 2,2,4-trimethyl-1,3 pentanediol diisobutyrate and/or derivatives thereof and/or spatial isomers thereof.

4. The composition according to claim 2, wherein said derivatives are esters, or salts, alcohols, ketones, ethers, aldehydes, sterols and amides of bis(2-ethylhexyl) adipate and 2,2,4-trimethyl 1,3 pentanediol diisobutyrate.

5. A method of repulsing arachnids said method comprising administering to an animal in need of such treatment a pharmaceutically acceptable amount of a composition according to claim 1 or 2.

6. A method of treating or preventing chicken mites or Northern fowl mites in hens, chickens and young chicks said method comprising administering to hens, chickens or young chicks in need of such treatment a pharmaceutically effective amount of a composition according to claim 1 or 2.

7. The method according to claim 5, wherein said composition comprises about 45.0% to 55.0% (w %/w %) bis(2-ethylhexyl) adipate and about 45.0% to 55.0% (w %/w %) 2,2,4-trimethyl-1,3 pentanediol diisobutyrate and/or derivatives thereof and/or isomers thereof and/or mixtures of bis(2-ethylhexyl) adipate or 2,2,4-trimethyl 1,3 pentanediol diisobutyrate with one or more esters, or salts, alcohols, ketones, ethers, aldehydes, sterols and amides derivatives of bis(2-ethylhexyl) adipate and 2,2,4-trimethyl 1,3 pentanediol diisobutyrate and/or with one or more isomers of bis(2-ethylhexyl) adipate and 2,2,4-trimethyl 1,3 pentanediol diisobutyrate and/or one or more isomers of the derivatives of bis(2-ethylhexyl) adipate and 2,2,4-trimethyl 1,3 pentanediol diisobutyrate.

8. The method according to claim 6, wherein said composition comprises about 45.0% to 55.0% (w %/w %) bis(2-ethylhexyl) adipate and about 45.0% to 55.0% (w %/w %) 2,2,4-trimethyl-1,3 pentanediol diisobutyrate and/or derivatives thereof and/or isomers thereof and/or mixtures of bis(2-ethylhexyl) adipate or 2,2,4-trimethyl 1,3 pentanediol diisobutyrate with one or more esters, or salts, alcohols, ketones, ethers, aldehydes, sterols and amides derivatives of bis(2-ethylhexyl) adipate and 2,2,4-trimethyl 1,3 pentanediol diisobutyrate and/or with one or more isomers of bis(2-ethylhexyl) adipate and 2,2,4-trimethyl 1,3 pentanediol diisobutyrate and/or one or more isomers of the derivatives of bis(2-ethylhexyl) adipate and 2,2,4-trimethyl 1,3 pentanediol diisobutyrate.

9. The method according to claim 5, wherein said administering comprises oral administration.

10. The method according to claim 6, wherein said administering comprises oral administration.

11. The method according to claim 7, wherein said administering comprises oral administration.

12. The method according to claim 5, wherein said administering comprises a topical administration.

13. The method according to claim 6, wherein said administering comprises a topical administration.

14. The method according to claim 7, wherein said administering comprises a topical administration.

15. A solution comprising the arachnids repulsive composition of claim 1.

16. A method of repulsing arachnids said method comprising administering to a human in need of such treatment a pharmaceutically acceptable amount of a composition according to claim 1 or 2.

17. The method according to claim 5, wherein said arachnid is a *Dermanyssus gallinae*, a tick or an *Ornithonyssus sylviarum*.

18. The method according to claim 16, wherein said arachnid is a *Dermanyssus gallinae*, a tick or an *Ornithonyssus sylviarum*.

19. The composition according to claim 1, wherein said derivatives are esters, or salts, alcohols, ketones, ethers, aldehydes, sterols and amides of bis(2-ethylhexyll) adipate and 2,2,4-trimethyl 1,3 pentanediol diisobutyrate.

20. A solution comprising the arachnids repulsive composition of claim 2.

21. The solution according to claim 15, wherein said solution comprises a nonaqueous solvent selected from the group consisting of alcohol, diethyl ether, chloroform, ethanol, benzene, propyl alcohol, isopropanol, 2-propanol and acetone polysorbate 80.

22. The solution according to claim 20, wherein said solution comprises a nonaqueous solvent selected from the group consisting of alcohol, diethyl ether, chloroform, ethanol, benzene, propyl alcohol, isopropanol, 2-propanol and acetone polysorbate 80.

23. The solution according to claim 15, wherein said solution comprises a solvent of water, or vegetal or animal oil.

24. The solution according to claim 20, wherein said solution comprises a solvent of water, or vegetal or animal oil.

25. The composition according to claim 1, comprising about 45.0% to 55.0% (w %/w %) bis(2-ethylhexyl) adipate and/or derivatives thereof, and about 45.0% to 55.0% (w %/w %) 2,2,4-trimethyl 1,3 pentanediol diisobutyrate and/or derivatives thereof, wherein said derivatives are esters, or salts, alcohols, ketones, ethers, aldehydes, sterols and amides of bis(2-ethylhexyl) adipate and 2,2,4-trimethyl 1,3 pentanediol diisobutyrate.

26. The composition according to claim 1, comprising about 45.0% to 55.0% (w %/w %) bis(2-ethylhexyl) adipate and about 45.0% to 55.0% (w %/w %) 2,2,4-trimethyl 1,3 pentanediol diisobutyrate.

27. The composition according to claim 2, wherein said derivatives are esters, or salts, alcohols, ketones, ethers, aldehydes, sterols and amides of bis(2-ethylhexyl) adipate and 2,2,4-trimethyl 1,3 pentanediol diisobutyrate.

28. The composition according to claim 2, or consisting of bis(2-ethylhexyl) adipate and 2,2,4-trimethyl 1,3 pentanediol diisobutyrate.

29. The composition according to claim 27, which consists of about 45.0% to 55.0% (w %/w %) bis(2-ethylhexyl) adipate and/or derivatives thereof, and about 45.0% to 55.0% (w %/w %) 2,2,4-trimethyl-1,3 pentanediol diisobutyrate and/or derivatives thereof.

30. The composition according to claim 28, which consists of about 45.0% to 55.0% (w %/w %) bis(2-ethylhexyl) adipate and about 45.0% to 55.0% (w %/w %) 2,2,4-trimethyl-1,3 pentanediol diisobutyrate.

\* \* \* \* \*